(12) United States Patent
Khan et al.

US007524820B1

(10) Patent No.: US 7,524,820 B1
(45) Date of Patent: *Apr. 28, 2009

(54) COMPOUNDS OF THERAPEUTIC VALUE IN THE TREATMENT OF MULTIPLE SCLEROSIS AND OTHER DISEASES WHEREIN FOAMY CELLS ARE INVOLVED IN THE DISEASE ETIOLOGY

(75) Inventors: Nisar A. Khan, Rotterdam (NL); Robbert Benner, Barendrecht (NL); Gert Wensvoort, Koekange (NL); Leonie A. Boven, Rotterdam (NL)

(73) Assignee: Biotempt B.V., Koekange (NL)

( * ) Notice: Subject to any disclaimer, the term of this patent is extended or adjusted under 35 U.S.C. 154(b) by 358 days.

This patent is subject to a terminal disclaimer.

(21) Appl. No.: 11/346,761

(22) Filed: Feb. 3, 2006

Related U.S. Application Data

(63) Continuation of application No. 11/286,571, filed on Nov. 23, 2005, now abandoned, which is a continuation-in-part of application No. 10/409,654, filed on Apr. 8, 2003, which is a continuation-in-part of application No. 10/028,075, filed on Dec. 21, 2001.

(51) Int. Cl.
*A61K 38/17* (2006.01)

(52) U.S. Cl. .......................................... 514/18; 514/12

(58) Field of Classification Search .................. None
See application file for complete search history.

(56) References Cited

U.S. PATENT DOCUMENTS

| | | | |
|---|---|---|---|
| 4,977,244 A | 12/1990 | Muchmore et al. | |
| 5,380,668 A | 1/1995 | Herron | |
| 5,677,275 A | 10/1997 | Lunardi-Iskandar et al. | |
| 5,851,997 A | 12/1998 | Harris | |
| 5,877,148 A | 3/1999 | Lunardi-Iskandar et al. | |
| 5,958,413 A | 9/1999 | Anagnostopulos et al. | |
| 5,968,513 A | 10/1999 | Gallo et al. | |
| 5,997,871 A | 12/1999 | Gallo et al. | |
| 6,319,504 B1 | 11/2001 | Gallo et al. | |
| 6,489,296 B1 | 12/2002 | Grinnell et al. | |
| 6,583,109 B1 | 6/2003 | Gallo et al. | |
| 6,596,688 B1 | 7/2003 | Gallo et al. | |
| 6,620,416 B1 | 9/2003 | Gallo et al. | |
| 6,727,227 B1 | 4/2004 | Khavinson | |
| 7,175,679 B2 * | 2/2007 | Khan et al. ............ | 514/2 |
| 2002/0041871 A1 | 4/2002 | Brudnak | |
| 2002/0064501 A1 | 5/2002 | Khan et al. | |
| 2003/0049273 A1 | 3/2003 | Gallo et al. | |
| 2003/0113733 A1 | 6/2003 | Khan et al. | |
| 2003/0119720 A1 | 6/2003 | Khan et al. | |
| 2003/0166556 A1 | 9/2003 | Khan et al. | |
| 2003/0186244 A1 | 10/2003 | Margus et al. | |
| 2003/0215434 A1 | 11/2003 | Khan et al. | |
| 2003/0219425 A1 | 11/2003 | Khan et al. | |
| 2003/0220257 A1 | 11/2003 | Benner et al. | |
| 2003/0220258 A1 | 11/2003 | Benner et al. | |
| 2003/0220259 A1 | 11/2003 | Benner et al. | |
| 2003/0220260 A1 | 11/2003 | Khan et al. | |
| 2003/0220261 A1 | 11/2003 | Khan et al. | |
| 2003/0224995 A1 | 12/2003 | Khan et al. | |
| 2004/0013661 A1 | 1/2004 | Wensvoort et al. | |

FOREIGN PATENT DOCUMENTS

| | | |
|---|---|---|
| DE | 3715662 | 11/1987 |
| DE | 19953339 | 5/2001 |
| EP | 1 138 692 A1 | 10/2001 |
| EP | 1 300 418 | 4/2003 |
| FR | 2 706 772 | 12/1994 |
| WO | 96/04008 | 2/1996 |
| WO | 97/49373 | 12/1997 |
| WO | 97/49418 | 12/1997 |
| WO | 97/49432 | 12/1997 |
| WO | WO 97/49721 | 12/1997 |
| WO | WO 98/35691 | 8/1998 |
| WO | WO 99/59617 | 11/1999 |
| WO | WO 01/10907 A2 | 2/2001 |
| WO | WO 01/11048 A2 | 2/2001 |
| WO | WO 01/29067 | 4/2001 |
| WO | WO 01/68113 A1 | 9/2001 |
| WO | WO 01/72831 | 10/2001 |
| WO | WO 02/085117 | 10/2002 |
| WO | WO 03/029292 A2 | 4/2003 |

OTHER PUBLICATIONS

Clerici et al., Journal of Neuroimmunology, 2001, vol. 121, pp. 88-101.*
Flores et al., Journal of Neuroimmunology, 2003, vol. 135, pp. 141-147.*
Albini et al., "Old drugs as novel angiogenesis inhibitors: Preclinical studies with NAC, hCG, EGCG and somatostatin," Clinical & Experimental Metastasis, 1999, pp. 739, vol. 17.
Blackwell et al., "The Role of Nuclear Factor-kB in Cytokine Gene Regulation," Am. J. Respir. Cell Mol. Biol., 1997, pp. 3-9, vol. 17.
Christman et al., "Nuclear factor kappaB: a pivotal role in the systemic inflammatory response syndrome and new target for therapy," Intens Care Med, 1998, pp. 1131-1138, vol. 24.

(Continued)

*Primary Examiner*—Christopher R. Tate
*Assistant Examiner*—Roy Teller
(74) *Attorney, Agent, or Firm*—TraskBritt

(57) ABSTRACT

The invention provides a method for assessing or determining activity of a test compound on modulation of gene product levels comprising culturing cells, contacting at least one of the cultured cells with a lipid-rich fraction, contacting at least one of the cultured cells with said test compound, determining the presence of a gene product of at least one cell of the cultured cells, and optionally determining the presence of the gene product of at least one cultured cell not contacted with said test compound. To assess human conditions most fully, it is preferred that the cell is of human origin, for example a peripheral blood monocyte taken from a healthy donor.

4 Claims, 2 Drawing Sheets

OTHER PUBLICATIONS

Connelly et al., "Biphasic Regulation of NF-kB Activity Underlies the Pro- and Anti-inflammatory Actions of Nitric Oxide," The Journal of Immunology, 2001, pp. 3873-3881, 166, The American Association of Immunologists, USA.

Friedlander, "Tackling anthrax," Nature, Nov. 8, 2001, pp. 160-161, vol. 414.

Jyonouchi et al., "Proinflammatory and regulatory cytokine production associated with innate and adaptive immune responses in children with autism spectrum disorders and developmental regression," J. Neuroim., 2001, pp. 170-179, vol. 120.

Kachra et al., "Low Molecular Weight Components but Not Dimeric HCG Inhibit Growth and Down-Regulate AP-1 Transcription Factor in Kaposi's Sarcoma Cells," Endocrinology, 1997, pp. 4038-4041, vol. 138, No. 9.

Kanungo et al., "Advanced Maturation of Heteropneustes Fossilis (Bloch) by Oral Administration of Human Chorionic Gonadotropin," J. Adv. Zool., 1999, pp. 1-5, vol. 20.

Keller et al., "Human Chorionic Gonadotropin (hCG) Is a Potent Angiogenic Factor for Uterine Endothelial Cells in Vitro," Placenta, Jul. 1999, pp. A37, vol. 20, No. 5-6.

Khan et al., "Inhibition of Diabetes in NOD Mice by Human Pregnancy Factor," Human Immunology, Dec. 2001, pp. 1315-1323, vol. 62, No. 12.

Khan et al., "Inhibition of Septic Shock in Mice by an Oligopeptide From the β-Chain of Human Chorionic Gonadotrophin Honnone," Human Immunology, Jan. 2002, pp. 1-7, vol. 63, No. 1.

Lang et al., "Induction of apoptosis in Kaposi's sarcoma spindle cell cultures by the subunits of human chorionic gonadtropin," AIDS, 1997, pp. 1333-1340, vol. 11, No. 11.

Lunardi-Iskandar et al., "Effects of a urinary factor from women in early pregnancy on HIV-a, SIV and associated disease," Nature Medicine, Apr. 1998, pp. 428-434, vol. 4, No. 4.

Medzhitov, "Toll-like Receptors and Innate Immunity," Nature Reviews/Immunology, Nov. 2001, pp. 135-145, vol. 1.

Muchmore et al., "Immunoregulatory Properties of Fractions from Human Pregnancy Urine: Evidence that Human Chorionic Gonadotropin is not Responsible," The Journal of Immunology, Mar. 1997, pp. 881-886, vol. 118, No. 3.

Muchmore et al., "Purification and Characterization of a Mannose-Containing Disaccharide Obtained from Human Pregnancy Urine," Journal of Experimental Medicine, Dec. 1984, pp. 1672-1685, vol. 160.

Patil et al., "The Study of the Effect of Human Chorionic Gonadotrophic (HCG) Hormone on the Survival of Adrenal Medulla Transplant in Brain. Preliminary Study," Acta Neurochir (Wien), 1987, pp. 76-78, vol. 87.

Rohrig et al., "Growth-stimulating Influence of Human Chorionic Gonadotropin (hCG) on *Plasmodium falciparum* in vitro," Zentralblatt Bakt, 1999, pp. 89-99, vol. 289.

Samaniego et al., "Induction of Programmed Cell Death in Kaposi's Sarcoma Cells by Preparations of Human Chorionic Gonadotropin," Journal of the National Cancer Institute, Jan. 20, 1999, pp. 135-143, vol. 91, No. 2.

Slater et al., "Decreased Mortality of Murine Graft-Versus-Host Disease by Human Chorionic gonadotropin," Transplantation, Jan. 1977, pp. 103-104, vol. 23, No. 1.

Tak et al., "NF-kappaB: a key role in inflammatory diseases," J Clin Invest., 2001, pp. 7-11, vol. 107.

Tan et al., "The role of activation of nuclear factor-kappa B of rat brain in the pathogenesis of experimental allergic encephalomyelitis," Acta Physiol Sinica, 2003, pp. 58-64, vol. 55.

Tovey et al., "Mucosal Cytokine Therapy: Marked Antiviral and Antitumor Activity," J. Interferon Cytokine Res., 1999, pp. 911-921, vol. 19.

Wulczyn et al., "The NF-kB/Rel and IkB gene families: mediators of immune response and inflammation," J. Mol. Med., 1996, pp. 749-769, vol. 74, No. 12.

Yamamoto et al., "Role of the NF-kB Pathway in the Pathogenesis of Human Disease States," Current Molecular Medicine, Jul. 2001, pp. 287-296, vol. 1, No. 3.

Ivanov et al., "Hemoglobin as a Source of Endogenous Bioactive Peptides: The Concept of Tissue-Specific Peptide Pool," Biopolymers, 1997, pp. 171-188, vol. 39.

Khavinson et al, Gerontological Aspects of Genome Peptide Regulation, 2005, S. Karger AG, Basel, Switzerland.

Khavinson et al., "Effects of Livagen Peptide on Chromatin Activation in Lymphocytes from Old People," Bulletin of Experimental Biology and Medicine, Oct. 2002, pp. 389-392, vol. 134, No. 4.

Khavinson et al., "Effects of Short Peptides on Lymphocyte Chromatin in Senile Subjects," Bulletin of Experimental Biology and Medicine, Jan. 2004, pp. 78-81, vol. 137, No. 1.

Khavinson et al., "Epithalon Peptide Induces Telomerase Activity and Telomere Elongation in Human Somatic Cells," Bulletin of Experimental Biology and Medicine, Jun. 2003, pp. 590-592, vol. 135, No. 6.

Khavinson et al., "Inductive Activity of Retinal Peptides," Bulletin of Experimental Biology and Medicine, Nov. 2002, pp. 482-484, vol. 134, No. 5.

Khavinson et al., "Mechanisms Underlying Geroprotective Effects of Peptides," Bulletin of Experimental Biology and Medicine, Jan. 2002, pp. 1-5, vol. 133, No. 1.

Khavinson et al., "Peptide Promotes Overcoming of the Division Limit in Human Somatic Cell," Bulletin of Experimental Biology and Medicine, May 2004, pp. 503-506, vol. 137, No. 5.

Morozov et al., "Natural and Synthetic Thymic Peptides as Therapeutics for Immune Dysfunction," Int. J. Immunophrmac., 1997, pp. 501-505, vol. 19, No. 9/10.

* cited by examiner

SEQUENCE LISTING

```
<160> NUMBER OF SEQ ID NOS: 27

<210> SEQ ID NO 1
<211> LENGTH: 4
<212> TYPE: PRT
<213> ORGANISM: Artificial
<220> FEATURE:
<223> OTHER INFORMATION: Synthetic peptide

<400> SEQUENCE: 1

Leu Gln Gly Val
1

<210> SEQ ID NO 2
<211> LENGTH: 4
<212> TYPE: PRT
<213> ORGANISM: Artificial
<220> FEATURE:
<223> OTHER INFORMATION: Synthetic peptide

<400> SEQUENCE: 2

Met Thr Arg Val
1

<210> SEQ ID NO 3
<211> LENGTH: 4
<212> TYPE: PRT
<213> ORGANISM: Artificial
<220> FEATURE:
<223> OTHER INFORMATION: Synthetic peptide
```

```
<400> SEQUENCE: 3

Ala Gln Gly Val
1

<210> SEQ ID NO 4
<211> LENGTH: 4
<212> TYPE: PRT
<213> ORGANISM: Artificial
<220> FEATURE:
<223> OTHER INFORMATION: Synthetic peptide

<400> SEQUENCE: 4

Leu Ala Gly Val
1

<210> SEQ ID NO 5
<211> LENGTH: 7
<212> TYPE: PRT
<213> ORGANISM: Artificial
<220> FEATURE:
<223> OTHER INFORMATION: Synthetic peptide

<400> SEQUENCE: 5

Val Leu Pro Ala Leu Pro Gln
1               5

<210> SEQ ID NO 6
<211> LENGTH: 6
<212> TYPE: PRT
<213> ORGANISM: Artificial
<220> FEATURE:
<223> OTHER INFORMATION: Synthetic peptide

<400> SEQUENCE: 6

Val Leu Pro Ala Leu Pro
1               5

<210> SEQ ID NO 7
<211> LENGTH: 20
<212> TYPE: DNA
<213> ORGANISM: Artificial
<220> FEATURE:
<223> OTHER INFORMATION: Forward primer for COX-2

<400> SEQUENCE: 7
ccttcctcct gtgcctgatg                                          20

<210> SEQ ID NO 8
<211> LENGTH: 22
<212> TYPE: DNA
<213> ORGANISM: Artificial
<220> FEATURE:
<223> OTHER INFORMATION: Reverse primer for COX-2

<400> SEQUENCE: 8
acaatctcat ttgaatcagg aa                                       22

<210> SEQ ID NO 9
<211> LENGTH: 22
<212> TYPE: DNA
<213> ORGANISM: Artificial
<220> FEATURE:
<223> OTHER INFORMATION: Probe for COX-2

<400> SEQUENCE: 9
tgcccgactc ccttgggtgt ca                                       22
```

<210> SEQ ID NO 10
<211> LENGTH: 18
<212> TYPE: DNA
<213> ORGANISM: Artificial
<220> FEATURE:
<223> OTHER INFORMATION: Forward primer for IL_10

<400> SEQUENCE: 10
acggcgctgt catcgatt                                           18

<210> SEQ ID NO 11
<211> LENGTH: 20
<212> TYPE: DNA
<213> ORGANISM: Artificial
<220> FEATURE:
<223> OTHER INFORMATION: Reverse primer for IL-10

<400> SEQUENCE: 11
ggcattcttc acctgctcca                                         20

<210> SEQ ID NO 12
<211> LENGTH: 27
<212> TYPE: DNA
<213> ORGANISM: Artificial
<220> FEATURE:
<223> OTHER INFORMATION: Probe for IL-10

<400> SEQUENCE: 12
cttccctgtg aaaacaagag caaggcc                                 27

<210> SEQ ID NO 13
<211> LENGTH: 20
<212> TYPE: DNA
<213> ORGANISM: Artificial
<220> FEATURE:
<223> OTHER INFORMATION: Forward primer for TNF-alpha

<400> SEQUENCE: 13
gcccaggcag tcagatcatc                                         20

<210> SEQ ID NO 14
<211> LENGTH: 21
<212> TYPE: DNA
<213> ORGANISM: Artificial
<220> FEATURE:
<223> OTHER INFORMATION: Reverse primer for TNF-alpha

<400> SEQUENCE: 14
gggtttgcta caacatgggc t                                       21

<210> SEQ ID NO 15
<211> LENGTH: 24
<212> TYPE: DNA
<213> ORGANISM: Artificial
<220> FEATURE:
<223> OTHER INFORMATION: Probe for TNF-alpha

<400> SEQUENCE: 15
ctcgaacccc gagtgacaag cctg                                    24

<210> SEQ ID NO 16
<211> LENGTH: 19
<212> TYPE: DNA
<213> ORGANISM: Artificial
<220> FEATURE:

```
<223> OTHER INFORMATION: Forward primer for PGES

<400> SEQUENCE: 16
caccggaacg acatggaga                                                   19

<210> SEQ ID NO 17
<211> LENGTH: 20
<212> TYPE: DNA
<213> ORGANISM: Artificial
<220> FEATURE:
<223> OTHER INFORMATION: Reverse primer for PGES

<400> SEQUENCE: 17
tccaggcgac aaaagggtta                                                  20

<210> SEQ ID NO 18
<211> LENGTH: 27
<212> TYPE: DNA
<213> ORGANISM: Artificial
<220> FEATURE:
<223> OTHER INFORMATION: Probe for PGES

<400> SEQUENCE: 18
tgggcttcgt ctactccttt ctgggtc                                          27

<210> SEQ ID NO 19
<211> LENGTH: 20
<212> TYPE: DNA
<213> ORGANISM: Artificial
<220> FEATURE:
<223> OTHER INFORMATION: Froward primer for IL-12p35

<400> SEQUENCE: 19
gcctggcctc cagaaagacc                                                  20

<210> SEQ ID NO 20
<211> LENGTH: 29
<212> TYPE: DNA
<213> ORGANISM: Artificial
<220> FEATURE:
<223> OTHER INFORMATION: Reverse primer for IL-12p35

<400> SEQUENCE: 20
acctggtaca tcttcaagtc ttcataaat                                        29

<210> SEQ ID NO 21
<211> LENGTH: 26
<212> TYPE: DNA
<213> ORGANISM: Artificial
<220> FEATURE:
<223> OTHER INFORMATION: Probe for IL-12p35

<400> SEQUENCE: 21
cttttatgat ggccctgtgc cttagt                                           26

<210> SEQ ID NO 22
<211> LENGTH: 21
<212> TYPE: DNA
<213> ORGANISM: Artificial
<220> FEATURE:
<223> OTHER INFORMATION: Forward primer for CCL18

<400> SEQUENCE: 22
gccaggagtt gtgagtttcc a                                                21
```

```
<210> SEQ ID NO 23
<211> LENGTH: 19
<212> TYPE: DNA
<213> ORGANISM: Artificial
<220> FEATURE:
<223> OTHER INFORMATION: Reverse primer for CCL18

<400> SEQUENCE: 23
tgcaaggccc ttcatgatg                                              19

<210> SEQ ID NO 24
<211> LENGTH: 24
<212> TYPE: DNA
<213> ORGANISM: Artificial
<220> FEATURE:
<223> OTHER INFORMATION: Probe for CCL18

<400> SEQUENCE: 24
tctgaccact tctctgcctg ccca                                        24

<210> SEQ ID NO 25
<211> LENGTH: 20
<212> TYPE: DNA
<213> ORGANISM: Artificial
<220> FEATURE:
<223> OTHER INFORMATION: Forward primer for IL-23p19

<400> SEQUENCE: 25
gttccccata tccagtgtgg                                             20

<210> SEQ ID NO 26
<211> LENGTH: 20
<212> TYPE: DNA
<213> ORGANISM: Artificial
<220> FEATURE:
<223> OTHER INFORMATION: Reverse primer for IL-23p19

<400> SEQUENCE: 26
tcctttgcaa gcagaactga                                             20

<210> SEQ ID NO 27
<211> LENGTH: 8
<212> TYPE: DNA
<213> ORGANISM: Artificial
<220> FEATURE:
<223> OTHER INFORMATION: Probe for IL-23p19

<400> SEQUENCE: 27 tggctgtg                                                           8
```

COMPOUNDS OF THERAPEUTIC VALUE IN THE TREATMENT OF MULTIPLE SCLEROSIS AND OTHER DISEASES WHEREIN FOAMY CELLS ARE INVOLVED IN THE DISEASE ETIOLOGY

CROSS-REFERENCE TO RELATED APPLICATIONS

This application is a continuation of U.S. patent application Ser. No. 11/286,571, filed Nov. 23, 2005, now abandoned, which is a continuation-in-part of U.S. patent application Ser. No. 10/409,654, filed Apr. 8, 2003, which is a continuation-in-part of U.S. patent application Ser. No. 10/028,075, filed Dec. 21, 2001, the contents of the entirety of each of which are incorporated by this reference.

TECHNICAL FIELD

The invention relates generally to the fields of biotechnology and medicine, and, more particularly, to the field of multiple sclerosis (MS) and other diseases wherein foamy cells are involved in the disease etiology.

BACKGROUND

Multiple sclerosis is a chronic inflammatory autoimmune disease of the central nervous system (CNS) and is characterized by the presence of demyelinated areas throughout the CNS. Various mechanisms leading to demyelination and axonal suffering have been implicated and the production of toxic inflammatory mediators by infiltrating and resident CNS macrophages is believed to play a pivotal role. MS is thought to be caused by a combined cellular and humoral autoimmune attack on myelin sheaths and possibly axons. Several facts have contributed to the concept that MS is an autoimmune disease, such as the association with various regulatory genes of the immune response, the presence of oligoclonal immunoglobulin species in CSF pointing to intrathecal expansion of specific B-cell clones, and the immunopathology of the lesions. Further support comes from the immunopathological similarity of MS with the autoimmune animal model EAE (experimental autoimmune/allergic encephalomyelitis) in rodents and primates, which, considering that no in vitro models exist is the only experimental model existing so far that may be used to test scientific hypotheses on the critical pathogenetic mechanisms and for the development of more effective therapies. However, the substantial dissimilarities between MS and EAE models have among others raised doubts about the autoimmune origin of MS. Notably, many of the EAE models present as a rapidly progressing monophasic disease with clinical and pathological findings that are more reminiscent of acute disseminated encephalomyelitis than chronic and relapsing MS. Although exceptions do exist, such as the elegant EAE model in Biozzi/ABH mice immunized with spinal-cord homogenate and a non-human-primate model for chronic MS in common marmosets that approximate the human disease better, currently no existing experimental model bridges the considerable gap between EAE models and MS.

Different subsets of myeloid cells are considered to have distinct roles in the development of MS. These distinct and specialized roles of myeloid cells depend on their origin and, importantly, their location. As such, perivascular cells appear to be optimally positioned for the modulation of infiltrating T cell activity whereas parenchymal myeloid cells may have a more prominent role in mechanisms involved in myelin breakdown and axonal suffering.

The plasticity and functional polarization of macrophages have received renewed attention in light of novel key properties of different forms of macrophages. Two extremes of a continuum have been identified for macrophages, being M1, or classically activated macrophages, and M2, or alternatively activated macrophages. The M1 phenotype is typically induced in vitro by IFN-gamma, TNF-alpha or LPS, whereas the M2 phenotype can be induced by IL-10, IL-4 or by the lipid mediator $PGE_2$, which is a strong inhibitor of pro-inflammatory immune responses. M1 macrophages are characterized by a high production of pro-inflammatory mediators and are involved in Th1 cell responses and killing of microorganisms and tumor cells. In contrast, M2 macrophages are associated with Th2 responses, scavenging of debris, promotion of tissue remodeling and repair and expression of anti-inflammatory molecules, including IL-1ra (IL-1 receptor antagonist) and CCL18. CCL18 in particular is a specific marker for human alternatively activated macrophages and is involved in immune suppression.

Demyelinating MS lesions are characterized by the presence of foamy macrophages, a characteristic subset of myeloid cells, which acquire their distinctive morphology by ingestion and accumulation of vast amounts of myelin-derived lipids. Foamy macrophages originate from both resident microglia and infiltrating monocytes, and about 30-80% of foamy macrophages in demyelinating lesions are blood-derived. Besides their apparent role in scavenging myelin, it is still poorly understood if and how foamy macrophages may affect the local inflammatory process. Since MS lesions are self-limiting and do not expand indefinitely it is likely that local mechanisms restrict CNS inflammation and may also promote tissue repair. It is however up to now not clear how these local mechanisms may function.

DISCLOSURE OF THE INVENTION

The invention provides a pharmaceutical composition for the treatment of a subject suffering from acute exacerbations believed to be due to MS, the pharmaceutical composition comprising a pharmacologically effective amount of LQGV (SEQ ID NO: 1), MTR, MTRV (SEQ ID NO: 2), AQGV (SEQ ID NO: 3), LAGV (SEQ ID NO: 4), AQG, LQG, VLPALPQ (SEQ ID NO: 5), LAG, and/or VLPALP (SEQ ID NO: 6) together with a pharmaceutically acceptable diluent. In particular, the invention provides a pharmaceutical composition for the treatment of a subject suffering from acute exacerbations believed to be due to MS, the pharmaceutical composition comprising a pharmacologically effective amount of LQGV (SEQ ID NO: 1), MTR, MTRV (SEQ ID NO: 2), AQGV (SEQ ID NO: 3), LAGV (SEQ ID NO: 4), AQG, and/or LQG together with a pharmaceutically acceptable diluent. More in particular, the invention provides a pharmaceutical composition for the treatment of a subject suffering from acute exacerbations believed to be due to MS, the pharmaceutical composition comprising a pharmacologically effective amount of LQGV (SEQ ID NO: 1), MTR, and/or MTRV together with a pharmaceutically acceptable diluent. Most in particular, the invention provides a pharmaceutical composition for the treatment of a subject suffering from acute exacerbations believed to be due to MS, the pharmaceutical composition comprising a pharmacologically effective amount of LQGV (SEQ ID NO: 1) together with a pharmaceutically acceptable diluent. A particularly useful pharmaceutically acceptable diluent is sterile water or an isotonic salt solution such as 0.9% saline or phosphate buffered salt (PBS). The peptide can be administered and introduced in-vivo preferably via any route, and via passage through the mucosae or skin. The peptide, or its modification or derivative, can be administered as the entity as such or as a pharmaceutically acceptable acid- or base-addition salt, formed by reaction with an inorganic acid (such as hydrochloric acid, hydrobromic acid, perchloric acid, nitric acid, thiocyanic acid, sulfuric acid, and phosphoric acid); or with an organic acid (such as formic acid, acetic acid, propionic acid, glycolic acid, lactic acid, pyruvic acid, oxalic acid, malonic acid, succinic acid, maleic acid, and fumaric acid); or by reaction with an inorganic base (such as sodium hydroxide, ammonium hydroxide, potassium hydroxide); or with an organic base (such as mono-, di-, trialkyl and aryl amines and substituted ethanolamines). A selected peptide and any of the derived entities may also be conjugated to DMSO, translocating peptides, sugars, lipids, other polypeptides, nucleic acids and PNA; and function in-situ as a conjugate or be released locally after reaching a targeted tissue or organ. The invention provides a method for the treatment of a, in particular human, subject believed to be suffering of multiple sclerosis, with a specific aim to reduce the frequency, and limit the lasting effects, of relapses or exacerbations, to relieve symptoms that arise from the release of additional pro-inflammatory cytokines during the relapse, to prevent disability arising from disease progression after the relapse, and promote tissue repair after the relapse. The invention provides a pharmaceutical composition for the oral treatment during relapses in case of relapsing/remitting multiple sclerosis occurring in a subject, in particular in a human, and a method for the (oral) treatment during the relapses of the exacerbations associated with additional pro-inflammatory cytokine release, for example in a primate suffering from MS or EAE comprising subjecting the subject to a pharmaceutical composition according to the invention. Herein, the invention provides a further selection of compounds useful for the treatment of MS and other diseases wherein foamy cells are involved in the disease etiology. Preferred compounds are LQGV (SEQ ID NO: 1), MTR, MTRV (SEQ ID NO: 2), AQGV (SEQ ID NO: 3), LAGV (SEQ ID NO: 4), AQG, LQG, VLPALPQ (SEQ ID NO: 5), LAG, and/or VLPALP (SEQ ID NO: 6). More preferred compounds are LQGV (SEQ ID NO: 1), MTR, MTRV (SEQ ID NO: 2), AQGV (SEQ ID NO: 3), LAGV (SEQ ID NO: 4), AQG, and LQG. Most preferred compounds are LQGV (SEQ ID NO: 1), MTR, and MTRV (SEQ ID NO: 2). Single most preferred compound is LQGV (SEQ ID NO: 1). Doses of 1 to 5 mg/kg bodyweight, for example every eight hours in a bolus injection or per infusionem until the patient stabilizes, are recommended initially, however, the potential of oral treatment allows a rapid transition to oral administration thereafter. For example in cases where large adverse response are expected or diagnosed, it is preferred to monitor cytokine profiles, such as TNF-alpha, IL-6 or IL-10 levels, in the plasma of the treated patient, and to stop treatment according to the invention when these levels are normal. In a preferred embodiment it is herein provided to give a patient experiencing a severe and acute exacerbation (relapse) with a bolus injection LQGV (SEQ ID NO: 1) or other peptide as provided herein at 0.1 to 30 mg/kg, preferably at 1 to 10 mg/kg, such as at 2 mg/kg and continue the infusion with LQGV (SEQ ID NO: 1) or another preferred peptide at a dose of 1 mg/kg bodyweight for every eight hours. The oral treatment commences, using dosages of 0.01 to 10 mg/kg bodyweight, and preferably 0.1 to 1 mg/kg bodyweight until the relapse has stabilized. Dosages may be increased or decreased, for example depending on the outcome of monitoring the cytokine profile in the plasma or CSF of the patient.

Of course, when the relapse seems of a milder nature, oral treatment is first choice to begin with. Although the peptide may be prepared by other methods known for the preparation of analogous compounds (e.g., by use of a solid phase synthesis), a method of making the peptide is described in the detailed description herein. During the process of preparation, solvents such as N,N-dimethylformamide (DMF), 1-butanol, 2-butanol, ethanol, methanol, ethyl acetate, methylene chloride, hexane, diethyl ether, water, acetic acid, and others may be used. Catalysts containing palladium or molybdenum may also be used in the preparation of the peptide.

However made, the peptide forms pharmacologically acceptable salts from pharmacologically acceptable organic and inorganic acids such as hydrochloric, hydrobromic, fumaric, phosphoric, ascorbic, tartaric, citric, lactic, maleic, palmitic, and other well-known acids. Especially preferred are the hydrochloric and acetic acid salts. The acid addition salts are obtained by reacting the peptide with the acid.

Methods of crystallizing compounds are described in Chase et al., Remington's Pharmaceutical Sciences, (16th ed., Mack Publishing Co., Easton, Pa., U.S.A., 1980) ("Remington's"), at page 1535.

A crystalline peptide can be used to make numerous dosage forms such as powders for insufflations, powders for reconstitution, tablet triturates (e.g., dispensing tablets and hypodermic tablets), other tablets, and so forth.

The pharmaceutical compositions containing the crystalline peptide are preferably dispensed in unit dosage forms, such as tablets, capsules, pills, powders, granules, suppositories, sterile parenteral solutions or suspensions and non-parenteral solutions or suspensions, containing suitable quantities of the pharmaceutically acceptable salt of the peptide.

Methods and compositions for making such dosage forms are well-known to those skilled in the art. For example, methods of making powders and their compositions are described at pages 1535 through 1552 of Remington's. Insufflations are described at page 1552, and insufflators are described at 1792. Methods and compositions for making tablets and pills, containing active ingredients, are described in Remington's, at pages 1553 through 1584. Methods of coating pharmaceutical dosage forms and making prolonged release pharmaceuticals are described at pages 1585-1613 of Remington's. The contents of these pages are hereby incorporated by this reference.

The crystalline peptide may also be incorporated into devices intended for implantation into a patient. Such devices, polymers intended for use therein, and methods of making both are described in U.S. Pat. Nos. 3,773,919, 4,767,628, and 4,675,189. For example, a sufficient quantity of the crystalline peptide could be incorporated into a PLAGA implant to allow for the release of peptide (e.g., 5 mg per day for one month) into the patient's body.

One advantage with pharmaceutical compositions containing the crystalline versus the amorphous product, is that the pharmaceutical composition containing the crystalline salt product, having twice the bioavailability of the amorphous product, may need only contain half the absolute amount of the active ingredient on certain mucosa thus decreasing the amount of ingredient needed to be insufflated or otherwise administered and decreasing the ultimate cost of the composition. Such mucosa would include the nasal and the buccal mucosa.

Although the pharmaceutical compositions containing the crystalline peptide may be formulated with adjuvants such as solubilizers, they need not be. The ability to use solely the crystalline peptide (i.e., the crystalline acid addition salt of the peptide) in a pharmaceutical composition to be applied to, for example, a nasal mucosa has advantages. For one thing, certain adjuvants are not suitable for chronic administration. However, long term administration may be necessary for the particular person ingesting the peptide. Another advantage is that the adjuvants necessarily take up a portion of the pharmaceutical composition, which portion may be better suited for the peptide in order to decrease mucosal discomfort.

However if it is desired, suitable solubilizers, buffers, swelling agents, etc., may be used in such formulations. Buffering agents are preferably those which keep the peptide in its unionized form.

The dosage of the crystalline acid addition salt/peptide administered will generally be dependent upon the kind of disorder to be treated, the type of patient involved, his age, health, weight, kind of concurrent treatment, if any, and length and frequency of treatment.

The dosage forms will be administered over varying durations. To treat a disorder, the compounds are administered to a patient for a length of time sufficient to alleviate the symptoms associated with the disorders that the patient is suffering from. This time will vary, but periods of time exceeding two months are especially preferred. After the symptoms have been alleviated, the compound may then be discontinued to determine whether it is still required by the particular patient.

Compounds were further selected in a method for assessing or determining activity of a test compound on modulation of gene product levels comprising culturing (preferably myeloid) cells, contacting at least one of the cultured cells with a lipid-rich fraction, contacting at least one of the cultured cells with the test compound, determining the presence of a gene product of at least one cell of the cultured cells, and optionally determining the presence of the gene product of at least one cultured cell not contacted with the test compound. To assess human conditions most fully, it is preferred that the cell is of human origin, for example a peripheral blood monocyte or granulocyte taken from a healthy donor. Also, the invention provides a method for assessing or determining activity of a test compound on modulation of gene product levels in more specific circumstances of disease, it is then preferred the myeloid cell has been derived from a subject thought to be suffering from a disease. Use of a method according to the invention would then allow for individualized medicine; test results indicating that a specific test compound has specific benefits for the subject may then be used for treatment of the subject against the disease.

Specific disease conditions that can be studied by a method according to the invention are those diseases wherein foamy cells are considered involved in the etiology of the disease, such as is the case with multiple sclerosis or atherosclerosis. These disease definition includes disease in which cells with a foam cell morphology have a modulatory function in either disease initiation, progress and aggravation, or in disease reduction, amelioration, inflammation control, tissue integrity-tissue homeostasis: thus not only multiple sclerosis (MS), but also disease other than MS, such as atherosclerosis (in the broad sense of the word, so including angina pectoris, myocardial infarction, stroke, vulnerable plaque syndrome), diabetes, lung disease in general (including chronic inflammation, asthma, emphysema, viral, bacterial, fungal and parasitic infection, as well as genetic aberrations such as cystic fibrosis, Pulmonary alveolar proteinosis, inflammatory bowel disease (IBD, including morbus Crohn and colitis ulcerosa), genetic deficiencies affecting lipid storage (e.g., Gaucher's disease) and Hodgkin's disease. The invention also provides a method to test efficacy or mechanism of action of candidate drugs or combinations of drugs for the disease of interest. It is herein also provided to use a method according to the invention as application of test system for individualized medicine; i.e., in diagnosis-prognosis studies, in assessment of individuals risk to develop disease related to foam cell (dys) function, wherein we here provide a method to predict disease risk, in conjunction with known risk factors (e.g., age, weight, gender, smoking for atherosclerosis). We can also now assess individual patient for their response to drug treatment in vitro, or ex vivo, and thus select the right patient-drug combination, and/or test combinations of drugs, and/or assess responsiveness of patient to establish dose to be used in treatment, e.g., by culturing relevant cell type(s) taken from peripheral blood of the individual in the presence of the appropriate source and form of foam cell inducing compound (I.e., myelin, oxLDL). By assessing drug response by titrating in the drug both during development of foam cells over a one to three day period, or when foam cells have been established will provide guidance in drug-selection.

Myeloid cells that can advantageously be used are derived from myeloid cell lines such as U937 (human): ATCC CRL-1593.2; THP-1 (human): ATCC TIB-202; RAW (mouse): ATCC TIB-71. In vitro foam cells are also cells having acquired a large bloated irregular morphology with multiple vesicles due to (excessive) lipid, glycolipid or sugar uptake, and/or increased intracellular production, and/or reduced degradation-catabolism of such compounds. As to the lipid-rich fraction to be used in a method according to the invention, it is preferred that the lipid-rich fraction comprises one or more compounds selected from the group of phospholipids cholesterol, sphingolipids, glycolipids, ceramides, such as can be found in myelin, for example in soluble form, or in particulate form being multiple membrane windings of oligodendrocyte extensions forming the multilamellar myelin sheath, or in particulate form being apoptotic cell bodies from oligodendrocytes, axons, neuron somata, astrocytes, microglia, and/or infiltrating white blood cells.

As to the detection of gene products involved, the invention for example provides a method for assessing or determining activity of a test compound on modulation of gene product levels comprising culturing myeloid cells, contacting at least one of the cultured cells with a lipid-rich fraction, contacting at least one of the cultured cells with the test compound, determining the presence of a gene product of at least one cell of the cultured cells, wherein the gene product is a proteinaceous substance such as a peptide, polypeptide or protein, having or not having been modified with post-translational modifications. Also, the invention provides a method wherein the gene product is a cytokine or chemokine. Gene products such as (m) RNA or specific parts thereof may also be detected, thereby allowing for identifying transcriptional activity in the cell that may or may not be influenced by the test compound under study. Again, a useful example of RNA testing comprises testing for RNA that at least partially encodes a cytokine or chemokine. Cell types preferably used in the invention are cells which have means to take up compounds from the environment by cell biological processes including micropinocytosis, macropinocytosis, phagocytosis are useful. In principle, under the appropriate tissue or culture conditions, many different cell types potentially acquire foam cell morphology and may be used. However, various cell types optimally equipped for phagocytosis are prime candidates for transformation into foam cells. These include for leukocytes: cell types from the myeloid and granulocyte series (monocytes-macrophages, neutrophils, eosinophils and basophils). Also, dendritic cells (DC) are a leukocyte subset also useful to the method. The origin of DC is disputed to some extent, with extensive debate on myeloid versus lymphoid DC, but clearly DC precursors are present in the circulation. DC can, for example, be generated in vitro from human monocytes and from bone marrow (mouse and human) in appropriate cytokine mixtures. Multiple sclerosis-associated cell types likely to turn into foam cells are microglia (brain macrophages) and infiltrating macrophages and DC. Also pericytes might be candidates. Neutrophils may be important in early lesions, and have phagocytic activity. Also rat, mouse, marmoset and rhesus monkeys cells (for which EAE-MS models have been established) develop into foam cells upon myelin exposure. For studying atherosclerotic disease it is useful to use macrophages or human monocytes to transform into foam cells mimicking those in the plaque, notably by uptake of oxLDL by means of scavenging receptors (SR-A, SR-B, CD36) and TLR (e.g., TLR4, TLR2). Other cell types to be considered are neutrophils, smooth muscle cells (SMC), fibroblasts and myofibroblasts. Prime candidates to study lung disease are alveolar macrophages and macrophages/phagocytes in the connective tissue of the lung. Other cell types to be considered are neutrophils, smooth muscle cells (SMC), fibroblasts, myofibroblasts, and type I and type II pneumocytes.

In particular, the invention provides a method to practice an in vitro model of MS. This method for example comprises a step of culturing a (preferably myeloid) cell or cells, preferably of human origin, such as a human blood monocyte obtained from a donor, if required differentiating the monocyte into other cell types such as macrophages and dendritic cells and a step of contacting the cultured cell with a lipid-rich fraction, preferably a phospholipid rich fraction, preferably with a myelin-rich fraction and a third step of culturing the cell in the presence of the lipid-rich fraction until the cell or at least 10% of the cells, preferably at least 20%, more preferably at least 30%, more preferably at least 30%, more preferably at least 40%, more preferably at least 50%, more preferably at least 60%, more preferably at least 70%, more preferably at least 80%, most preferably at least 90%, have developed a foamy characteristic because of the ingestion of the lipid-rich fraction, as can be observed by light microscope or as can be determined by staining the cell or cells for the intracellular presence of lipid-rich fractions, as for example can be done by staining the cell or cells or a fraction thereof with a stain for the detection of neutral lipids, such as by staining with oil red O histochemistry (ORO) or by fluorescent labeling of lipids with DiI and subsequent detection of ingested fluorescent lipids. Letting foam cells stand in culture for a too long period without feeding a lipid-rich fraction will make them return to a non-foamy character; it then suffices to re-feed them a lipid-rich fraction to induce the foamy morphology again. In one embodiment of the invention, human myeloid cells obtained from healthy donors are fed with 10 to 200, preferably with about 50 microg/ml human myelin for example purified from postmortem brain. In another embodiment of the invention, mouse primary macrophages obtained from healthy mice are fed with 10 to 200, preferably with about 50 microg/ml human or mouse myelin. In another embodiment of the invention, marmoset myeloid cells obtained from healthy donors are fed with 10 to 200, preferably with about 50 microg/ml marmoset myelin. In another embodiment of the invention, human primary macrophages obtained from healthy donors are fed with 10 to 200, preferably with about 50 microg/ml phospholipid. Although small individual changes in kinetics between individual donors may be observed, myeloid cells acquire a foamy morphology between 24 and 48 hours and contain a markedly increased number and size of lipid droplets in comparison to control cells (i.e., not fed with lipid) as for example demonstrated by ORO staining. Lipid droplets in cells not exposed to myelin likely derive from lipid in the culture medium and/or apoptotic other macrophages in the culture. Primary macrophages may be used but also myeloid or monocyte-like cells or cell lines such as U937 (human): ATCC CRL-1593.2; THP-1 (human): ATCC TIB-202; RAW (mouse): ATCC TIB-71, or specific monocyte-like cells such as rodent, marmoset or human myeloid dendritic cells (mDC) or microglial cells can develop the foamy characteristics when fed lipid-rich fraction and are advantageously used in a method as provided herein.

We hypothesized that foamy macrophages in MS brain are anti-inflammatory M2-type macrophages as generated under laboratory conditions. We then hypothesized that foamy macrophages actively contribute to the resolution of brain inflammation. Our findings reveal an important and previously overlooked anti-inflammatory role for foamy macrophages in MS lesions. The invention provides the insight that multiple sclerosis (MS) lesion activity concurs with the extent of inflammation, demyelination and axonal suffering, in short, with the balance between local pro- and anti-inflammatory activities. Pro-inflammatory myeloid cells contribute to lesion development, but the self-limiting nature of lesions now is explained as earlier unidentified anti-inflammatory mechanisms. We show herein that lipid ingestion, and in particular myelin ingestion by myeloid cells induces a foamy appearance and confers anti-inflammatory function. We show that myelin-containing foam cells in MS lesions consistently express a series of anti-inflammatory molecules while mainly lacking pro-inflammatory cytokines. Unique location-dependent cytokine and membrane receptor expression profiles allow for functional specialization allowing for differential responses to micro-environmental cues. The invention therewith provides a novel, and advantageously an essentially human in vitro model of MS using foamy macrophages wherein it functionally is confirmed that in human macrophages myelin ingestion induces an anti-inflammatory program, to which program the effects of test compounds can be evaluated. The invention also provides novel insights into the mechanisms of lesion control and opens new roads to therapeutic intervention at the exact site where it most counts in MS, the recurrent inflammatory lesion in the brain.

DETAILED DESCRIPTION OF THE INVENTION

Figure 1:
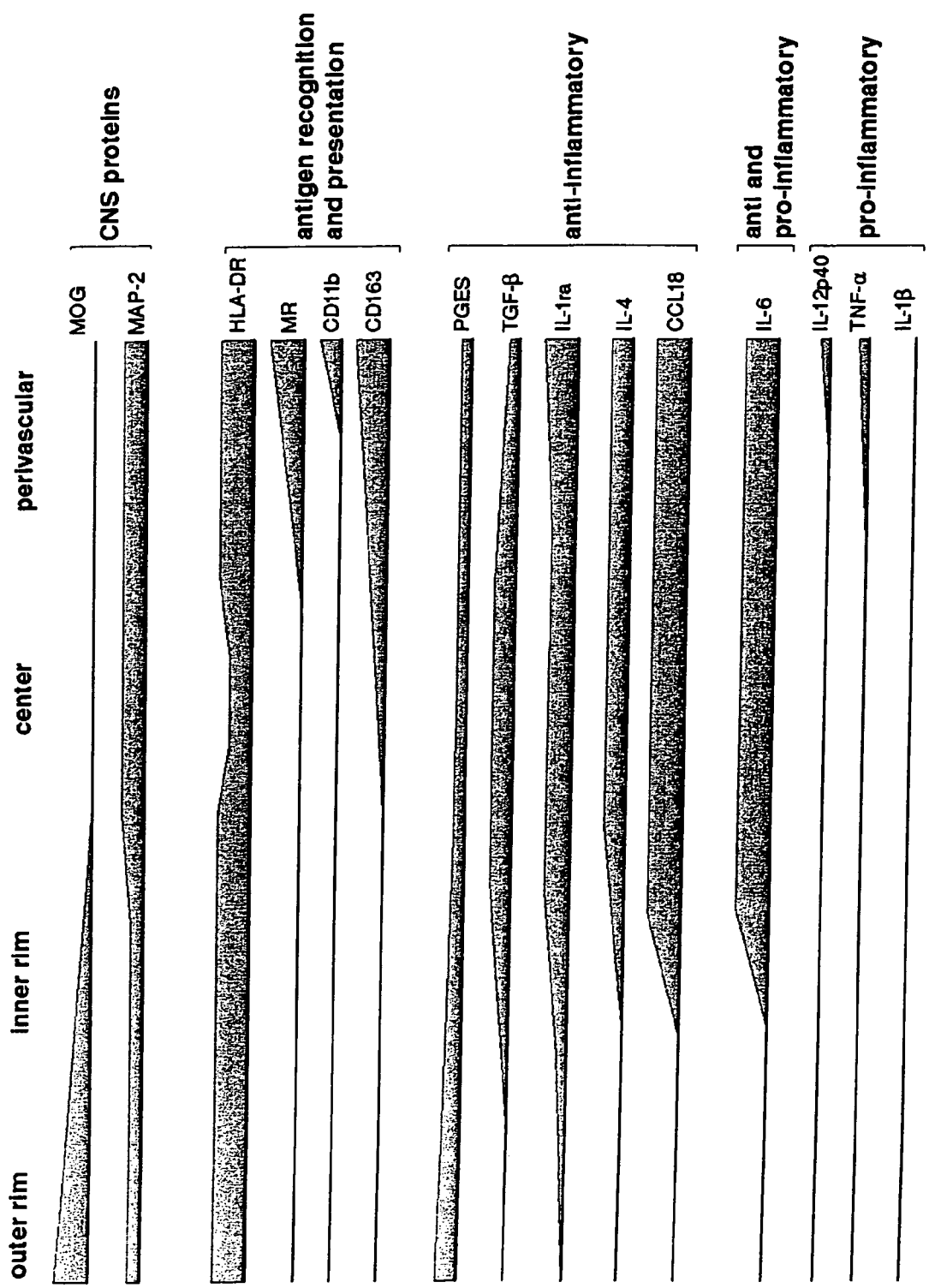
FIG. 1: Microlocation-dependent expression profiles of surface and intercellular molecules by foamy macrophages in MS lesions. The presence of CNS proteins, molecules involved in antigen recognition and presentation, as well as anti- and pro-inflammatory molecules was analyzed for foamy macrophages at different sites within the lesion, i.e., in the outer rim, the inner rim, its lesion center and in perivascular spaces. Quantification was based on frequency of positive foamy macrophages and staining intensity and was performed on two to three lesions from four different MS patients. The gradient between lesion center and the perivascular space reflects increasing or decreasing staining frequency and/or intensity towards the perivascular compartment.
Figure 2:
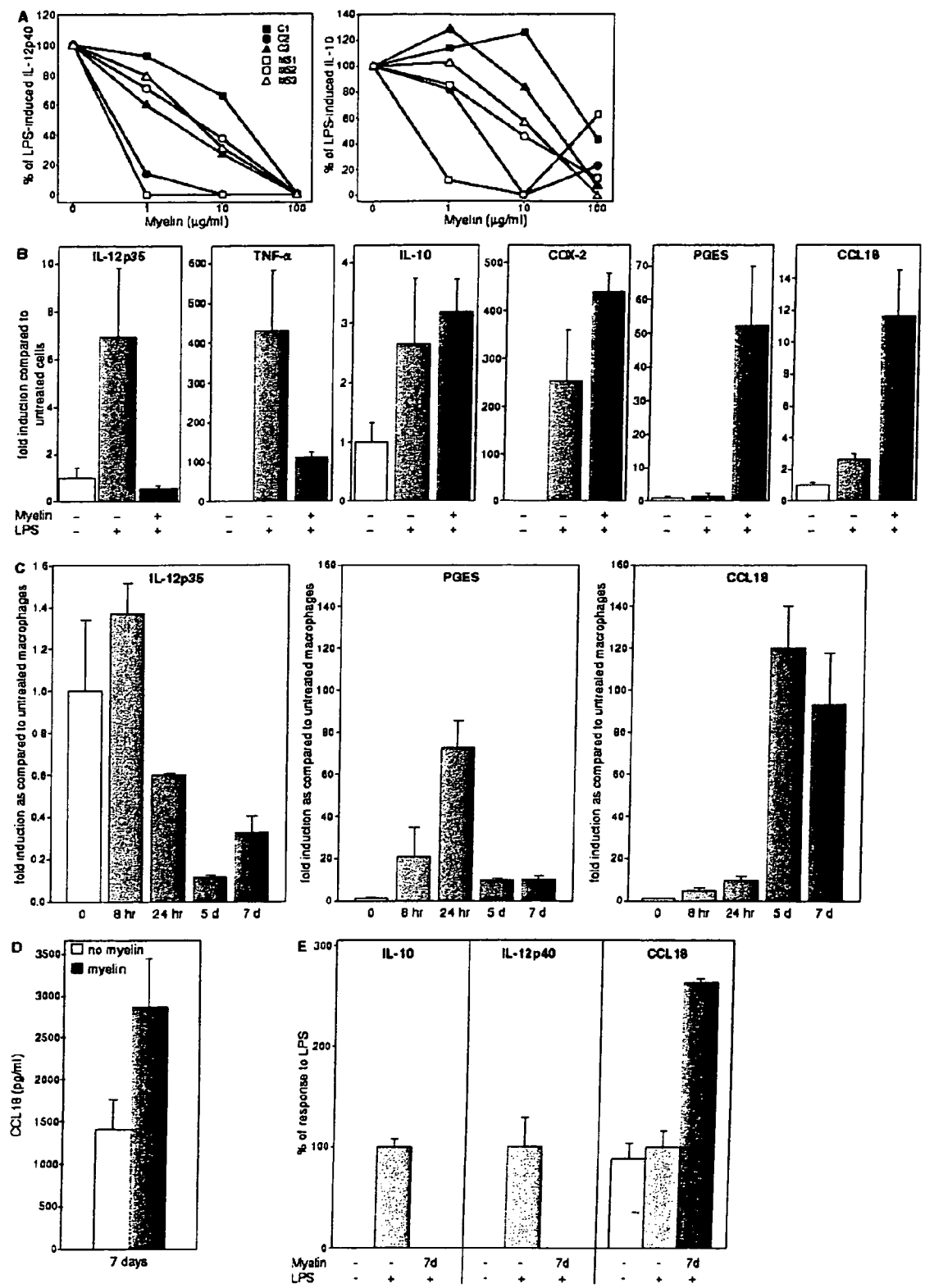
FIG. 2: Foamy macrophages in vitro are immunosuppressive. (a) Foamy macrophages were generated using myelin preparations derived from brain tissue of three control individuals and three MS patients. After addition of 1 ng/ml LPS for 24 hours cytokine levels in the supernatants were determined. LPS-induced IL-12p40 and IL-10 production was dose-dependently inhibited by myelin and is shown as the percentage of production by untreated LPS-stimulated macrophages. Control patient-derived myelin, filled squares; MS patient-derived myelin, open squares. (b) Foamy macrophages were incubated with myelin for 24 hours and subsequently stimulated with 1 ng/ml LPS for two hours where indicated. LPS-induced IL-12p35 and TNF-alpha mRNA levels were significantly inhibited in foamy macrophages compared to control macrophages. LPS-induced IL-10 and COX-2 were not affected. PGES and CCL18 mRNA expression was not induced significantly by LPS and was0 increased by myelin. *, P<0.05 compared with LPS-treated macrophages. (c) Over time, foamy macrophages showed a decreased, but not significant, IL-12p35 mRNA expression. In addition there was a transient increase in PGES and a sustained increase in CCL18 mRNA expression. *, P<0.05 compared with untreated control macrophages. (d) This was paralleled on protein level as seven days after myelin addition foamy macrophages still showed significantly increased CCL18 production. *, P<0.05 compared with untreated control macrophages. (e) Seven days after myelin ingestion foamy macrophages showed a complete inhibition of LPS-induced IL-10 and IL-12p40 production and a three-fold induction of CCL18 production. *, P<0.05 compared with LPS-treated macrophages. All data shown are representative for at least two independent experiments using different blood donors. Results are expressed as mean±s.d.

The peptides LQGV (SEQ ID NO: 1), MTR, MTRV (SEQ ID NO: 2), AQGV (SEQ ID NO: 3), LAGV (SEQ ID NO: 4), AQG, LQG, VLPALPQ (SEQ ID NO: 5), LAG, and VLPALP (SEQ ID NO: 6) as mentioned herein were prepared by solid-phase synthesis using the fluorenylmethoxycarbonyl (Fmoc)/tert-butyl-based methodology with 2-chlorotrityl chloride resin as the solid support. The side-chain of glutamine was protected with a trityl function. The peptides were synthesized manually. Each coupling consisted of the following steps: (i) removal of the alpha-amino Fmoc-protection by piperidine in dimethylformamide (DMF), (ii) coupling of the Fmoc amino acid (3 eq) with diisopropylcarbodiimide (DIC)/1-hydroxybenzotriazole (HOBt) in DMF/N-methylformamide (NMP) and (iii) capping of the remaining amino functions with acetic anhydride/diisopropylethylamine (DIEA) in DMF/NMP. Upon completion of the synthesis, the peptide resin was treated with a mixture of trifluoroacetic acid (TFA)/H$_2$O/triisopropylsilane (TIS) 95:2.5:2.5. After 30 minutes, TIS was added until decolorization. The solution was evaporated in vacuo and the peptide precipitated with diethyl ether. The crude peptides were dissolved in water (50-100 mg/ml) and purified by reverse-phase high-performance liquid chromatography (RP-HPLC). HPLC conditions were: column: Vydac TP21810C18 (10×250 mm); elution system: gradient system of 0.1% TFA in water v/v (A) and 0.1% TFA in acetonitrile (ACN) v/v (B); flow rate 6 ml/min; absorbance was detected from 190-370 nm. There were different gradient systems used. For example for peptides LQG and LQGV (SEQ ID NO: 1): ten minutes 100% A followed by linear gradient 0-10% B in 50 minutes. For example for peptides VLPALP (SEQ ID NO: 6) and VLPALPQ (SEQ ID NO: 5): five minutes 5% B followed by linear gradient 1% B/minute. The collected fractions were concentrated to about 5 ml by rotation film evaporation under reduced pressure at 40° C. The remaining TFA was exchanged against acetate by eluting two times over a column with anion exchange resin (Merck II) in acetate form. The elute was concentrated and lyophilized in 28 hours. Peptides later were prepared for use by dissolving them in PBS.

Abbreviations Used

LPS, lipopolysaccharide; IL, Interleukin; PGE prostaglandin E; EAE, experimental autoimmune encephalomyelitis; Th, T helper; ATCC American Type Culture Collection; IL-1ra, receptor antagonist; HLA human leukocyte antigen; TGF transforming growth factor; ELISA enzyme-linked immuno sorbent assay; COX cyclooxygenase; TNF, tumor necrosis factor; IFN interferon; MS Multiple sclerosis; CNS Central nervous system; NAWM Normal appearing white matter; MOG Myelin oligodendrocyte glycoprotein; ORO Oil red O;

TABLE I

Markers and antibodies.

| Molecule/marker | Function |
|---|---|
| IL-1ra | Anti-inflammatory, Endogenous IL-1 antagonist |
| IL-4 | Anti-inflammatory |
| PGES | Anti-inflammatory |
| TGF-beta | Anti-inflammatory |
| CCL18 | expressed by T/B cells, DC, macrophages, chemotactic to naïve T cells and iDC |
| HLA class II | Antigen presentation to CD4+ T cells |
| CD163 | Scavenger receptor for haptoglobin-haemoglobin complexes, anti-inflammatory actions |
| Mannose receptor | Lectin, recognition of micro-organisms |
| CD11b | Forms complement receptor 3 with CD18 |
| IL-1beta | Pro-inflammatory cytokine |
| TNF-alpha | Pro-inflammatory cytokine |
| IL-6 | Pro- and anti-inflammatory actions |
| IL-12 p40/p70 | Pro-inflammatory cytokine |
| MOG | Myelin oligodendrocyte glycoprotein |
| MAP-2 | Neuronal protein |

The invention is further explained with the aid of the following illustrative examples.

EXAMPLE 1

Myelin-Laden Macrophages are Anti-Inflammatory Consistent with Foam Cells in Multiple Sclerosis Material and Methods Immunohistochemical Analysis of Postmortem MS Brain Tissue Human autopsy brain tissue from five MS patients was provided by the Netherlands Brain Bank in Amsterdam. Immunohistochemistry was performed on frozen sections of MS brain tissue to detect expression of (anti-)inflammatory markers and CNS antigens (Table 1) as described previously (Hoefakker et al., 1995). In brief, 6 μm frozen sections were cut and thawed on to glass slides. Slides were kept overnight at room temperature in humidified atmosphere. After air-drying, slides were fixed in acetone containing 0.02% (v/v) H$_2$O$_2$. Slides were then air-dried for ten minutes, washed with PBS and incubated with optimally diluted primary antibody overnight at 4° C. in humidified atmosphere. Incubations with secondary rabbit anti-mouse-Ig-biotin (Dako) and tertiary horseradish peroxidase (HRP)-labeled avidin-biotin-complex (ABC/HRP: Dako) were performed for one hour at RT. HRP activity was revealed by incubation for ten minutes at RT with 3-amino-9-ethyl-carbazole (AEC: Sigma), leading to a bright red precipitate. After washing, sections were counterstained with hematoxylin, and embedded with glycerol-gelatin. Omission of primary antibody acted as control staining. Myelin degradation products were detected with oil-red O (ORO), which stains neutral lipids, as previously described (Chayen and Bitensky, 1991). The used antibodies were the anti-inflammatory markers IL-1ra (Biosource), IL-4 (U-Cytech), PGES (Cayman), TGF-beta (Santa Cruz), and CCL18 (R&D); for antigen recognition and presentation HLA class II (Dako), CD163, mannose receptor, CD11b (BD biosciences); as pro-inflammatory markers IL-1beta (gift from Dr. Boraschi), TNF-alpha (U-Cytech), IL-6 (Genzyme), IL-12p40/p70 (Pharmingen); for CNS proteins MOG, MAP-2 (Pierce).

In Vitro Model for Myelin-Driven Foam Cell Formation

Myelin was isolated as described previously (Norton and Poduslo, 1973). In short, white matter derived from post-mortem brain tissue was homogenized in 0.32 M sucrose and subsequently layered on 0.85 M sucrose. After centrifugation at 75,000 g myelin was collected from the interface, washed in water and suspended in water for osmotic shock. Using this method, the purified myelin was shown to be free of any recognizable fragments of other subcellular elements. Previous studies have shown that purified myelin structurally resembled the whole multilamellar myelin structure surrounding as seen in tissue sections using electron microscopy (Autilio et al., 1964).

Peripheral blood mononuclear cells were isolated from heparinized blood from healthy donors using a Ficoll density gradient. Subsequently, monocytes were purified using Percoll density gradient resulting in >80% monocytes. Monocytes were cultured in suspension at a concentration of $1\times10^6$ cells/ml in TEFLON® flasks (Nalgene) in RPMI with 5% human AB serum. After five to seven days, monocyte-derived macrophages were recovered from the Teflon flasks and seeded in tissue culture plates. After 24 hours, non-adherent cells were removed and remaining cells were >95% macrophages as determined by macrophage-specific esterase staining. Foamy macrophages were generated in vitro by incubating macrophages with myelin for 24 hours to seven days (referred to as one day and seven day-old foamy macrophages). In most experiments, 50 microg/ml myelin was used. Control macrophages were obtained from the same donor, and not fed with myelin.

ELISA

To determine cytokine production in culture supernatants of foamy macrophages commercial capture ELISA was performed. TNF-alpha, IL-10 and IL-12p40 were measured in the collected culture supernatants. ELISA was performed according to the manufacturers' guidelines (Biosource). Briefly, polystyrene microtiter wells (Immuno Maxisorp) were coated overnight at 4° C. with monoclonal anti-cytokine capture antibodies. Wells were blocked for two hours at RT with PBS/0.5% BSA, followed by washing (0.9% NaCl/0.1% Tween20). Freshly thawed supernatants of the cell cultures and recombinant human cytokine-standards were incubated in duplicates for two hours at RT in the presence of a biotinylated second anti-cytokine detection antibody. After washing, wells were incubated with HRP-labeled poly-streptavidin (CLB) for 30 minutes at RT. HRP revelation was performed with 3,3',5,5'-tetramethylbenzidine (TMB) peroxidase (KPL). Color development was stopped by adding equal volume of 1M $H_2SO_4$. Optical density was measured at 450 nm.

CCL18 levels were measured by sandwich ELISA assay using a commercially available CytoSet (Biosource), consisting of a capture-antibody, a biotinylated detection-antibody, recombinant CCL18 standard and streptavidin-HRP conjugate. Assay conditions were exactly as described by the manufacturer.

Real-Time Quantitative PCR

To quantify mRNA expression by foamy macrophages total RNA was extracted from cell cultures using the GenElute Mammalian Total RNA kit (Sigma). RNA samples were treated with DNAse I (Invitrogen) to remove any contaminating DNA. Using 1 microg of the total RNA as template, copy DNA (cDNA) was prepared using the AMV Reverse Transcription System (Promega). To determine target gene mRNA expression, real-time quantitative reverse-transcription-PCR was performed using TaqMan technology (PE-Applied Biosystems) as described previously (van der Fits et al., 2003). Target gene expression levels were corrected for GAPDH mRNA levels. Sequences of the PCR primers (PE Biosystems), and fluorogenic probes (Eurogentec) are: forward primer 5'CCTTCCTCCTGTGCCTGATG (SEQ ID NO: 7), reverse primer 5'ACAATCTCATTTGAATCAG-GAA (SEQ ID NO: 8), probe 5'TGCCCGACTCCCT-TGGGTGTCA (SEQ ID NO: 9) for COX-2; forward primer 5'ACGGCGCTGTCATCGATT (SEQ ID NO: 10), reverse primer 5'GGCATTCTTCACCTGCTCCA (SEQ ID NO: 11), probe 5'CTTCCCTGTGAAAACAAGAGCAAGGCC (SEQ ID NO: 12) for IL-10; forward primer 5'GCCCAGGCAGT-CAGATCATC (SEQ ID NO: 13), reverse primer 5'-GGGTTTGCTACAACATGGGCT (SEQ ID NO: 14), probe 5'CTCGAACCCCGAGTGACAAGCCTG (SEQ ID NO: 15) for TNF-α; forward primer 5'CACCGGAACGA-CATGGAGA (SEQ ID NO: 16), reverse primer 5'TCCAG-GCGACAAAAGGGTTA (SEQ ID NO: 17), probe 5'TGGGCTTCGTCTACTCCTTTCTGGGTC (SEQ ID NO: 18) for PGES; forward primer 5'GCCTGGCCTCCAGAAA-GACC (SEQ ID NO: 19), reverse primer 5'ACCTGGTA-CATCTTCAAGTCTTCATAAAT (SEQ ID NO: 20), probe 5'CTTTTATGATGGCCCTGTGCCTTAGT (SEQ ID NO: 21) for IL-12p35; forward primer 5'GCCAGGAGTTGT-GAGTTTCCA (SEQ ID NO: 22), reverse primer 5'-TG-CAAGGCCCTTCATGATG (SEQ ID NO: 23), probe 5'TCT-GACCACTTCTCTGCCTGCCCA (SEQ ID NO: 24) for CCL18, forward primer 5'-GTTCCCCATATCCAGTGTGG (SEQ ID NO: 25), reverse primer 5'-TCCTTTGCAAGCA-GAACTGA (SEQ ID NO: 26), probe TGGCTGTG (SEQ ID NO: 27, Roche) for IL-23p19.

Statistical Analysis

Statistical analysis was performed using the non-parametric Mann-Whitney analysis. P values <0.05 were considered significant.

Multiple sclerosis (MS) is a chronic inflammatory autoimmune disease of the central nervous system (CNS) and is characterized by the presence of demyelinated areas throughout the CNS (Sospedra and Martin, 2005). Various mechanisms leading to demyelination and axonal suffering have been implicated and the production of toxic inflammatory mediators by infiltrating and resident CNS macrophages is believed to play a pivotal role (Becher et al., 2000; Cannella and Raine, 2004; Lassmann, 2004; Matute and Perez-Cerda, 2005; Raine, 1994; Sospedra and Martin, 2005; Wingerchuk et al., 2001).

Different subsets of myeloid cells have distinct roles in the development of experimental autoimmune encephalomyelitis (EAE), an animal model for MS. These distinct and specialized roles of myeloid cells depend on their origin and, importantly, their location (Greter et al., 2005; Heppner et al., 2005; McMahon et al., 2005; Platten and Steinman, 2005). As such, perivascular cells appear to be optimally positioned for the modulation of infiltrating T cell activity whereas parenchymal myeloid cells may have a more prominent role in mechanisms involved in myelin breakdown and axonal suffering (Platten and Steinman, 2005).

The plasticity and functional polarization of macrophages have received renewed attention in light of novel key properties of different forms of macrophages. Two extremes of a continuum have been identified for macrophages, being M1, or classically activated macrophages, and M2, or alternatively activated macrophages (Gordon, 2003; Mantovani et al., 2004; Mantovani et al., 2002; Mosser, 2003). The M1 phenotype is typically induced in vitro by IFN-gamma, TNF-alpha or LPS, whereas the M2 phenotype can be induced by IL-10, IL-4 or by the lipid mediator $PGE_2$, which is a strong inhibitor of pro-inflammatory immune responses (Gratchev et al., 2001; Harris et al., 2002; Hinz et al., 2000; Ikegami et al., 2001; Kalinski et al., 1997). M1 macrophages are characterized by a high production of pro-inflammatory mediators and are involved in Th1 cell responses and killing of micro-organisms and tumor cells. In contrast, M2 macrophages are associated with Th2 responses, scavenging of debris, promotion of tissue remodeling and repair and expression of anti-inflammatory molecules, including IL-1ra (IL-1 receptor antagonist) and CCL18 (Gordon, 2003; Mantovani et al., 2004). CCL18 in particular is a specific marker for human alternatively activated macrophages (Goerdt et al., 1999; Gordon, 2003; Kodelja et al., 1998; Mantovani et al., 2002) and is likely involved in immune suppression. Demyelinating MS lesions are characterized by the presence of foamy macrophages, a characteristic subset of myeloid cells, which acquire their distinctive morphology by ingestion and accumulation of vast amounts of myelin-derived lipids. Foamy macrophages originate from both resident microglia and infiltrating monocytes. 30-80% of foamy macrophages in demyelinating lesions are estimated to be blood-derived (Li et al., 1996). Besides their apparent role in scavenging myelin, it is still poorly understood if and how foamy macrophages may affect the local inflammatory process. Since MS lesions are self-limiting and do not expand indefinitely it is likely that local mechanisms restrict CNS inflammation and may also promote tissue repair. We hypothesized that foamy macrophages are anti-inflammatory M2-type macrophages and actively contribute to the resolution of brain inflammation and hence to tissue integrity and function. Our findings reveal an important and previously overlooked anti-inflammatory and modulatory role for foamy macrophages in MS lesions.

RESULTS OF EXAMPLE 1

Foamy Macrophages Express Anti-Inflammatory Markers and Demonstrate a Unique Location-Dependent Phenotype To determine the immune phenotype of lipid-laden foamy macrophages in MS lesions, we used antibodies against CNS proteins, various surface markers involved in antigen recognition and presentation, and pro- and anti-inflammatory markers characteristic for M1 and M2 macrophages (Goerdt et al., 1999; Gordon, 2003; Kodelja et al., 1998; Mantovani et al., 2002). Foamy macrophages were defined by their characteristic morphology, strong HLA-DR expression and presence of neutral lipids, which are detected by oil red O histochemistry (ORO). To determine whether foamy macrophages display phenotypic and functional specialization dependent on micro-location, we analyzed the phenotype of these cells in different micro-locations. We distinguished between foamy macrophages within the lesion, in perivascular spaces within the lesion and in the outer or inner rim. The distinction between the outer and inner rim was based on the presence of neutral lipids, MOG and on the size of the foamy macrophages. Outer rim foamy macrophages were smaller in size and contained more MOG, but less neutral lipids than inner rim foamy macrophages.

IL-6, a cytokine with pro-as well as anti-inflammatory properties as well as the anti-inflammatory M2 marker IL-1ra and prostaglandin $E_2$ synthase (PGES) were differentially expressed in the distinct areas of an MS-lesion. Whereas IL-6 and IL-1ra were detected mostly in perivascular and lesional foamy macrophages, PGES was mostly expressed in the outer, and to a lesser extent in the inner rim. Importantly, expression patterns between cells varied even when cells were in close proximity. Mannose receptor, which is characteristic for M2 macrophages (Gordon, 2003; Mantovani et al., 2004; Mantovani et al., 2002; Mosser, 2003), was highly expressed on foamy macrophages in perivascular spaces but was mostly absent on parenchymal foamy macrophages. Occasionally, a weakly positive cell was observed which was always in the vicinity of a blood vessel. TGF-beta expression showed the reverse expression pattern with more pronounced expression by parenchymal foamy macrophages compared to perivascular foamy macrophages.

As hypothesized, the relative levels of expression were related to specific micro-locations within the lesion. Foamy macrophages in the lesion rim contained MOG, and immunoreactivity showed a decreasing trend towards the center of the lesion, possibly reflecting time-dependent myelin degradation. In contrast, intracellular neuronal antigen MAP-2 immunoreactivity increased towards the center of the lesion, implicating that neuronal damage occurs mostly in the lesion center. Only foamy macrophages within perivascular spaces expressed the surface markers CD11b, CD163 and mannose receptor. The anti-inflammatory molecules IL-1ra, CCL18, IL-10, TGF-beta and IL-4 were all strongly expressed by foamy macrophages, and expression was highest in the center of the lesion. Interestingly, IL-10 expression was absent on foamy macrophages in perivascular spaces. The pro-inflammatory cytokines TNF-alpha, IL-1beta, IL-12p40/70 were not expressed by foamy macrophages in any of the micro-locations, whereas cells associated with vessels in normal appearing white matter (NAWM) did express these pro-inflammatory cytokines. Phenotypic heterogeneity was not observed among non-foamy macrophages which were present in low numbers in perivascular spaces in NAWM.

Thus, we demonstrate that foamy macrophages in the brain have clear anti-inflammatory characteristics, resemble M2 macrophages, and have a unique phenotype depending on the micro-location.

Myelin Induces a Foamy Morphology in Macrophages Resembling that of Foamy Macrophages In Situ Next, we set out to determine whether ingestion of myelin in vitro results in an anti-inflammatory function of foamy macrophages as observed in situ. Therefore, we first developed a fully human in vitro model of foamy macrophages. In short, human monocyte-derived macrophages are cultured in the absence or presence of human brain-derived myelin for 24 hours. Whereas cells cultured in the absence of myelin did not appear foamy (at magnification 32×), those cultured with myelin acquire a characteristic foamy morphology as observed by light microscopy. Human primary macrophages obtained from healthy donors were fed with 50 microg/ml human myelin and changes in the morphology were monitored by light microscopy and by ORO staining to detect intracellular neutral lipids. Although small individual changes in kinetics between individual donors were observed, macrophages acquired a foamy morphology between 24 and 48 hours and contained a markedly increased number and size of lipid droplets in comparison to control macrophages (i.e., not fed with myelin) as demonstrated by ORO staining. The typical foamy morphology of macrophages could still be observed one week upon the initial addition of myelin. Macrophage viability was not affected by myelin ingestion when a dose range of 1-100 microg/ml as was used, as was demonstrated by trypan blue staining.

Foamy Macrophages do not Mount Pro-Inflammatory Responses to Prototypical Inflammatory Stimuli and Produce Anti-Inflammatory Mediators To assess the effect of myelin ingestion on macrophage function, cytokine levels were determined in supernatants of myelin-laden macrophages before and after LPS stimulation. Since variation in myelin lipid composition between MS and normal brain has been reported (Woelk and Borri, 1973), myelin was isolated from white matter of three control brains and three MS brains to investigate possible functional differences. Macrophages were incubated with the distinct myelin preparations for 24 hours and IL-10 and IL-12p40 levels were determined in the supernatants by ELISA. None of the myelin preparations induced IL-12p40 and only the highest dose of one MS brain-derived myelin was associated with a transient IL-10 induction. All myelin preparations inhibited LPS-induced IL-12p40 and IL-10 induction in a dose-dependent fashion. No significant differences were observed in cytokine production between foamy macrophages generated using the different myelin preparations. For subsequent experiments 50 microg/ml myelin was used.

Next, the effect of myelin ingestion on LPS-induced mRNA levels of different pro- and anti-inflammatory mediators was determined. Macrophages were incubated with myelin for 24 hours and subsequently stimulated with LPS for an additional two hours, after which RNA was isolated and real time RT-PCR was performed for IL-12p35, TNF-alpha, IL-10, COX-2, PGES and CCL18. LPS-induced IL-12p35 and TNF-alpha expression by foamy macrophages was completely inhibited. IL-10 was slightly but not significantly induced by LPS in control macrophages as well as foamy macrophages. COX-2 was increased after LPS stimulation in control macrophages but this induction was not significantly inhibited in foamy macrophages. Foamy macrophages showed between 15-50 and 8-12-fold induction of CCL18 and PGES compared to control macrophages. Thus, myelin ingestion resulted in a differential modulation of LPS responses. LPS-induced IL-12p40 and TNF-alpha expression was strongly and significantly inhibited, IL-10 and COX-2 expression remained unaffected and the expression of anti-inflammatory CCL18 and PGES significantly increased.

To determine whether myelin ingestion results in long-term modulation of macrophage function, macrophages were incubated with myelin for the indicated time periods and real time RT-PCR was performed for IL-12p35, IL-10, PGES and CCL18. IL-10 mRNA was not detectable at any time point. After myelin uptake IL-12p35 expression was decreased, albeit not significantly, over time in comparison to control macrophages. In contrast to IL-12p35 both PGES and CCL18 were induced by myelin. Seven day-old foamy macrophages expressed 10- and 90-fold more PGES and CCL18 than control macrophages. IL-12p40, IL-10, and CCL18 levels were subsequently determined in supernatants of these foamy macrophages. CCL18 is constitutively produced by macrophages and production by foamy macrophages is increased at day 7 after myelin ingestion, paralleling the increased CCL18 mRNA expression by foamy macrophages. IL-12p40 and IL-10 were not detectable.

Subsequently we determined whether the aberrant LPS response persisted over time. Seven days after initial myelin ingestion foamy macrophages were stimulated with 1 ng/ml LPS for 24 hours and cytokine levels in the supernatant were determined by ELISA. LPS-induced IL-12p40 and IL-10 production by these foamy macrophages was abolished completely whereas CCL18 was significantly increased. In addition, responses to other prototypical pro-inflammatory stimuli such as peptidoglycan and zymosan were also completely abolished.

The relapsing-remitting nature of MS strongly suggests the presence of potent counter-regulatory mechanisms that keep the disease in check. One such mechanism may be the active control of inflammation in the CNS itself thus preventing infinite expansion of the demyelinating lesion. Inflammation and demyelination are responsible for at least short-term neurological symptoms. Inflammation probably contributes to axonal loss as neurons are more vulnerable to environmental insults when the protective myelin sheaths are destroyed and the axons exposed (Grigoriadis et al., 2004; Kuhlmann et al., 2002). It is therefore imperative that in the developing lesions the production of toxic molecules is halted and that inflammation is limited allowing for tissue repair (Sospedra and Martin, 2005). Myelin-laden foamy macrophages are abundantly present in demyelinating lesions and although it is generally assumed that these cells contribute to inflammation, evidence for this is scarce (van der Laan et al., 1996). This lack of data on foamy macrophage function in MS is in sharp contrast with the increasing attention for foam cells in atherosclerosis (Greaves and Gordon, 2005) reporting potent immune-regulatory functions by lipids and lipid-induced molecules (Harris et al., 2002; Joseph et al., 2004; Joseph et al., 2003; Lawrence et al., 2002; Pettus et al., 2002). Lipid-laden cells are anti-inflammatory (Lawrence et al., 2002) and it was shown that low-density lipoprotein (LDL) uptake by macrophages inhibits TNF-induced TNF expression and induces IL-10 (Ares et al., 2002; Lo et al., 1999; Varadhachary et al., 2001). Foamy macrophages in the rim of active demyelinating lesions have been shown to contain plasma LDL (Newcombe et al., 1994).

Here, we establish that foamy macrophages in active MS lesions have consistent immunosuppressive function, while displaying a unique surface phenotype dependent on the micro-location. In addition, we demonstrate that ingestion of human myelin alters human macrophage function in vitro by inducing anti-inflammatory molecules and by inhibiting responses to pro-inflammatory stimuli. The results presented here reveal a new regulatory pathway in MS.

We demonstrate that foamy macrophages in demyelinating lesions in MS brain express various markers that are involved in anti-inflammatory processes, including IL-1ra, IL-10, CCL18, TGF-alpha, and that a subset of the foamy macrophages express markers involved in innate immunity, including mannose receptor and CD163. These molecules are all characteristic for alternatively activated M2 macrophages (Gordon, 2003; Mantovani et al., 2002; Mosser, 2003) and this strongly suggests a local regulatory immunosuppressive role. Importantly, our data show that foamy macrophages occur in discrete subsets. This may reflect their origin (i.e., microglial-derived vs. blood-derived), their age and the degree of lipid degradation, and most likely the cues received from their microenvironment. These cues include the type of ingested lipids, cytokine environment, presence and identity of neighboring cells or signals from the extracellular matrix. The unique combination of surface and intracellular molecules of individual macrophages in different areas of the lesion suggests that they are likely to exert diverse functions depending on their location. Foamy MOG-positive macrophages in the lesion rim may be more involved in phagocytosis of myelin whereas foamy macrophages inside the lesion appear to be geared for down-regulation of inflammation as suggested by high expression of anti-inflammatory cytokines. Interestingly, our in vitro data show a transient increase in PGES expression and a sustained increase in CCL18 expression. This parallels the in situ analysis showing highest expression of PGES in foamy macrophages in the lesion rim that likely have ingested myelin more recently than foamy CCL18-positive macrophages in the lesion center. IL-10 was expressed in situ mostly by lesional foamy macrophages. In vitro IL-10 is transiently induced by myelin, but LPS-induced IL-10 production is inhibited. This suggests complex regulation of IL-10 expression both in vitro and in vivo which will need to be explored in more detail in future studies. Regulatory foamy macrophages in perivascular spaces are likely to affect the function of newly infiltrating cells. Current experiments employ genomic as well as well as biochemical approaches to identify such immunomodulating mechanisms.

We show here that the observed functional phenotype of foamy macrophages in MS lesions results from the accumulation of lipids derived from myelin and phagocytozed apoptotic cell membranes, in concert with local microenvironmental cues, such as differences in extracellular matrix content in the perivascular infiltrate versus the lesion in the brain parenchyma. Foamy macrophages demonstrate a phenotype resembling that of anti-inflammatory M2 macrophages, are likely to contribute to resolution of inflammation, and may therefore be responsible for inhibiting further lesion development and promoting lesion repair. In addition, they may also function as a first line of defense against infiltrating inflammatory myeloid cells. Future studies are required to elucidate which lipid components are able to regulate macrophage function and which mechanisms are involved. Understanding the mechanisms behind naturally occurring counter-regulatory processes allows for definition of new cellular targets for therapeutic drug design for the treatment of MS and even has broader applications for other foam cell-associated diseases including atherosclerosis and lung-conditions.

EXAMPLE 2

Determining Whether Compounds Modulate Responses by Macrophages and Foam Cells

Experimental Design:
Human monocyte-derived macrophages were cultured in medium (=macrophages) or in the presence of human brain-derived myelin for 48 hours (=foam cells).

Macrophages and foam cells were cultured in the presence of 10 microg/ml compounds LAGV (SEQ ID NO: 4), AQGV (SEQ ID NO: 3), LAG, AQG, MTR, MTRV (SEQ ID NO: 2), VLPALPQ (SEQ ID NO: 5), VLPALP (SEQ ID NO: 6), LQGV (SEQ ID NO: 1), LQG (see for example PCT International Publication No. WO 03/029292 A2 (published Apr. 10, 2003), PCT International Publication No. WO 01/72831 A2 (published Oct. 4, 2001), PCT/EP2004/003747, and U.S. Patent Application Publications 20020064501 A1 (published May 30, 2002), 20030119720 A1 (published Jun. 26, 2003), 20030113733 A1 (published Jun. 19, 2003), US 2003/0220259 A1 (published Nov. 27th, 2003) and 20030166556 A1 (published Sep. 4, 2003), the contents of all of which are incorporated by this reference) for three hours.

10 ng/ml LPS was added to the cultures for an additional 16 hours.

Supernatants were collected and ELISA performed for TNF-alpha, IL-12p40, and IL-10.

Results:

Protein Levels are Depicted in Table 2

LPS induced TNF-alpha, IL-12p40 and IL-10 in macrophages as expected, confirming the experimental system performed as usual.

Foam cells demonstrated decreased LPS responses for IL-10 and IL-12p40 as expected. LPS-induced TNF-alpha production by foam cells was not affected as has been observed before.

Effects of compounds on LPS responses are shown in Table 1.

The compounds did not affect macrophage or foam cell morphology or viability as judged by microscopic examination.

EXAMPLE 3

Determining Whether Compounds Affect Cytokine Production by Human Macrophages and Foam Cells Experimental Design:

Human monocyte-derived macrophages from a healthy blood bank donor were cultured in medium (=macrophages) or in the presence of human brain-derived myelin for 48 hours (=foam cells).

Macrophages and foam cells were cultured in duplicate in the presence of 10 microg/ml of compounds LAGV (SEQ ID NO: 4), AQGV (SEQ ID NO: 3), LAG, AQG, MTR, MTRV (SEQ ID NO: 2), VLPALPQ (SEQ ID NO: 5), VLPALP (SEQ ID NO: 6), LQGV (SEQ ID NO: 1), LQG for two or eight hours, or cultured in macrophage medium with vehicle.

Cells were lysed and real time RT-PCR (TaqMan technology) was performed on all samples for GAPDH (housekeeping gene), TNF-alpha. (pro-inflammatory), IL-12p35 (pro-inflammatory), IL-10 (anti-inflammatory), CCL18 (chemokine), COX-2 (prostaglandin pathway).

Results:

Effects of Compounds on mRNA Expression Levels are Depicted in Tables 2, 3 and 4.

The compounds did not affect macrophage or foam cell morphology or viability as judged by microscopic examination.

cDNA quality of two samples was not sufficient for reliable semi-quantification. Values of these samples (#6, peptides two hours on macrophages; # 10, peptides eight hours on foam cells) have been omitted.

EXAMPLE 4

Determining Whether Foam Cells Differentially Express Chemokines Compared to Control Macrophages Experimental Design:

Human monocyte-derived macrophages from a healthy blood bank donor were cultured in medium (=macrophages) or in the presence of human brain-derived myelin for 48 hours (=foam cells)

10 microg/ml of the compounds LAGV (SEQ ID NO: 4), AQGV (SEQ ID NO: 3) or LQGV (SEQ ID NO: 1) is added to macrophages or foam cells for six hours, or macrophages or foam cells are cultured in macrophage medium with vehicle.

Cells were lysed, RNA isolated and Affymetrix microarray (U133+2 chip with 53.675 transcripts) was used according to the manufacturer's instructions to determine relative mRNA levels Results:

Effect of Myelin Ingestion and Additional Effect of the Compounds LAGV (SEQ ID NO: 4), AQGV (SEQ ID NO: 3) or LQGV (SEQ ID NO: 1) on Eight Different Selected Chemokines is Depicted in Table 6

Compounds did not affect the chemokine expression by control macrophages

EXAMPLE 5

The efficiency of ten different peptides was testes in four assays (as described in examples 1 and 2). Peptides were ranked in order of efficiency, with 1 being the effect considered to be most beneficial for MS patients (i.e., low TNF, high IL-10, high CCL18) and 10 being the most detrimental (i.e., high TNF, low IL-10, low CCL18). For each peptide the mean ranking was calculated. The peptide with the highest overall ranking (i.e., the lowest number) is the most potent peptide with regards to the induction of effects which can be considered beneficial for MS patients. Results are shown in Table 7.

TABLE 2

LPS-induced cytokine responses by compounds tested in human macrophages and in foam cells

| compound | mean macrophages | Mean foam cells | sd macrophages | sd foam cells |
|---|---|---|---|---|
| | TNF-alpha (pg/ml) | | | |
| None | 21664 | 29366 | 2532 | 2733 |
| LAGV (SEQ ID NO: 4) | 8336 | 16464 | 322 | 2331 |
| AQGV (SEQ ID NO: 3) | 9075 | 15895 | 1688 | 723 |
| LAG | 13281 | 15895 | 2009 | 5225 |
| AQGV (SEQ ID NO: 3) | 14475 | 14531 | 482 | 563 |
| MTR | 13054 | 15839 | 2170 | 5626 |
| MTRV (SEQ ID NO: 2) | 14816 | 19249 | 3697 | 804 |
| VLPALPQ (SEQ ID NO: 5) | 13167 | 20101 | 402 | 563 |

TABLE 2-continued

LPS-induced cytokine responses by compounds tested in human macrophages and in foam cells

| compound | mean macrophages | Mean foam cells | sd macrophages | sd foam cells |
|---|---|---|---|---|
| VLPALP (SEQ ID NO: 6) | 10723 | 20670 | 4823 | 6189 |
| LQGV (SEQ ID NO: 1) | 5381 | 13565 | 1125 | 482 |
| LQG | 4812 | 16691 | 643 | 884 |
| | IL-10 (pg/ml) | | | |
| None | 4140 | 485 | 118 | 29 |
| LAGV (SEQ ID NO: 4) | 2203 | 222 | 358 | 29 |
| AQGV (SEQ ID NO: 3) | 2977 | 186 | 105 | 0 |
| LAG | 2793 | 191 | 65 | 2 |
| AQGV (SEQ ID NO: 3) | 2078 | 179 | 110 | 0 |
| MTR | 2399 | 206 | 18 | 2 |
| MTRV (SEQ ID NO: 2) | 3105 | 235 | 251 | 11 |
| VLPALPQ (SEQ ID NO: 5) | 3004 | 229 | 107 | 16 |
| VLPALP (SEQ ID NO: 6) | 2654 | 153 | 11 | 20 |
| LQGV (SEQ ID NO: 1) | 3654 | 572 | 96 | 13 |
| LQG | 4209 | 601 | 172 | 22 |
| | IL-12p40 (pg/ml) | | | |
| None | 2258 | 1320 | | |
| LAGV (SEQ ID NO: 4) | 2038 | 1100 | | |
| AQGV (SEQ ID NO: 3) | 1527 | 1093 | | |
| LAG | 1799 | 899 | | |
| AQGV (SEQ ID NO: 3) | 1942 | 997 | | |
| MTR | 1910 | 912 | | |
| MTRV (SEQ ID NO: 2) | 2325 | 804 | | |
| VLPALPQ (SEQ ID NO: 5) | 1901 | 1218 | | |
| VLPALP (SEQ ID NO: 6) | 2426 | 1284 | | |
| LQGV (SEQ ID NO: 1) | 3364 | 1274 | | |
| LQG | 1859 | 1742 | | |

TABLE 3

Taqman results

| | CCL18 peptide treatment 2h | mean | s.d. | CCL18 peptide treatment 8h | mean | s.d. |
|---|---|---|---|---|---|---|
| macrophages | None | 0.99 | 0.45 | none | 1.14 | 0.29 |
| | LAGV (SEQ ID NO: 4) | 1.00 | 0.13 | LAGV (SEQ ID NO: 4) | 1.28 | 0.50 |
| | AQGV (SEQ ID NO: 3) | 1.11 | 0.39 | AQGV (SEQ ID NO: 3) | 2.42 | 0.16 |
| | LAG | 1.70 | 0.52 | LAG | 1.29 | 0.14 |
| | AQG | 1.00 | 0.43 | AQG | 1.91 | 0.25 |
| | MTR | ND | | MTR | 1.46 | 0.20 |
| | MTRV (SEQ ID NO: 2) | 1.74 | 0.14 | MTRV (SEQ ID NO: 2) | 1.13 | 0.39 |
| | VLPALPQ (SEQ ID NO: 5) | 2.50 | 0.32 | VLPALPQ (SEQ ID NO: 5) | 0.98 | 0.48 |
| | VLPALP (SEQ ID NO: 6) | 1.31 | 0.20 | VLPALP (SEQ ID NO: 6) | 2.20 | 0.48 |
| | LQGV (SEQ ID NO: 1) | 2.41 | 1.04 | LQGV (SEQ ID NO: 1) | 2.29 | 0.53 |
| | LQG | 1.33 | 0.31 | LQG | 1.91 | 0.10 |
| foam cells | None | 278.87 | 99.48 | none | 21.07 | 3.08 |
| | LAGV (SEQ ID NO: 4) | 886.13 | 353.99 | LAGV (SEQ ID NO: 4) | 81.82 | 9.06 |
| | AQGV (SEQ ID NO: 3) | 600.00 | 211.58 | AQGV (SEQ ID NO: 3) | 52.94 | 11.11 |
| | LAG | 219.51 | 33.08 | LAG | 92.32 | 31.57 |
| | AQG | 355.94 | 81.34 | AQG | 118.82 | 29.83 |

TABLE 3-continued

Taqman results

| CCL18 peptide treatment 2h | mean | s.d. | CCL18 peptide treatment 8h | mean | s.d. |
|---|---|---|---|---|---|
| MTR | 262.81 | 65.57 | MTR | 124.05 | 24.11 |
| MTRV (SEQ ID NO: 2) | 277.78 | 94.19 | MTRV (SEQ ID NO: 2) | 42.65 | 0.00 |
| VLPALPQ (SEQ ID NO: 5) | 205.43 | 46.94 | VLPALPQ (SEQ ID NO: 5) | 49.25 | 3.90 |
| VLPALP (SEQ ID NO: 6) | 278.99 | 2.01 | VLPALP (SEQ ID NO: 6) | 55.00 | 16.88 |
| LQGV (SEQ ID NO: 1) | 488.87 | 38.70 | LQGV (SEQ ID NO: 1) | ND | |
| LQG | 153.76 | 8.86 | LQG | 32.86 | 8.42 |

TABLE 4

Taqman results

| | COX-2 peptide treatment 2h | mean | s.d. | COX-2 peptide treatment 8h | mean | s.d. |
|---|---|---|---|---|---|---|
| macrophages | None | 0.591211 | 0.226438 | none | 0.94 | 0.32 |
| | LAGV (SEQ ID NO: 4) | 1.28552 | 0.590098 | LAGV (SEQ ID NO: 4) | 1.47 | 1.33 |
| | AQGV (SEQ ID NO: 3) | 1.009161 | 0.171062 | AQGV (SEQ ID NO: 3) | 0.71 | 0.03 |
| | LAG | 1.047836 | 0.344225 | LAG | 1.42 | 0.10 |
| | AQG | 1.28199 | 0.434554 | AQG | 1.58 | |
| | MTR | ND | | MTR | 2.40 | 1.05 |
| | MTRV (SEQ ID NO: 2) | 1.321293 | 0.966936 | MTRV (SEQ ID NO: 2) | 0.71 | 0.39 |
| | VLPALPQ (SEQ ID NO: 5) | 1.01643 | 0.301701 | VLPALPQ (SEQ ID NO: 5) | 0.50 | 0.15 |
| | VLPALP (SEQ ID NO: 6) | 1.03924 | 0.186638 | VLPALP (SEQ ID NO: 6) | 0.65 | 0.10 |
| | LQGV (SEQ ID NO: 1) | 0.577613 | 0.104948 | LQGV (SEQ ID NO: 1) | 0.67 | 0.12 |
| | LQG | 0.673839 | 0.100383 | LQG | 2.27 | 2.00 |
| foam cells | None | 0.89199 | 0.159893 | none | 0.79 | 0.09 |
| | LAGV (SEQ ID NO: 4) | 0.912541 | 0 | LAGV (SEQ ID NO: 4) | 2.19 | 0.46 |
| | AQGV (SEQ ID NO: 3) | 0.763449 | 0.203646 | AQGV (SEQ ID NO: 3) | 2.31 | 0.28 |
| | LAG | 0.722072 | 0.2582 | LAG | 1.66 | 0.50 |
| | AQG | 1.081277 | 0.053871 | AQG | 1.77 | 0.30 |
| | MTR | 0.73216 | 0.14501 | MTR | 2.48 | 0.01 |
| | MTRV (SEQ ID NO: 2) | 1.445971 | 0 | MTRV (SEQ ID NO: 2) | 2.15 | 0.53 |
| | VLPALPQ (SEQ ID NO: 5) | 0.690174 | 0 | VLPALPQ (SEQ ID NO: 5) | 1.15 | 0.07 |
| | VLPALP (SEQ ID NO: 6) | 1.013483 | 0.109235 | VLPALP (SEQ ID NO: 6) | 1.44 | 1.46 |
| | LQGV (SEQ ID NO: 1) | 0.805138 | 0.046792 | LQGV (SEQ ID NO: 1) | ND | |
| | LQG | 0.556831 | 0.159653 | LQG | 0.88 | 0.63 |

TABLE 5

Taqman results

| | IL-10 peptide treatment 2h | mean | s.d. | IL-10 peptide treatment 8h | mean | s.d. |
|---|---|---|---|---|---|---|
| macrophages | None | 0.838719 | 0.084748 | none | 0.96 | 0.23 |
| | LAGV (SEQ ID NO: 4) | 0.93201 | 0.073727 | LAGV (SEQ ID NO: 4) | 1.25 | 0.31 |
| | AQGV (SEQ ID NO: 3) | 1.078281 | 0.162801 | AQGV (SEQ ID NO: 3) | 1.97 | 0.17 |
| | LAG | 0.949998 | 0.155105 | LAG | 1.14 | 0.10 |
| | AQG | 0.794645 | 0.120295 | AQG | 1.28 | 0.23 |
| | MTR | ND | | MTR | 1.56 | 0.77 |
| | MTRV (SEQ ID NO: 2) | 0.799543 | 0.059873 | MTRV (SEQ ID NO: 2) | 0.83 | 0.20 |
| | VLPALPQ (SEQ ID NO: 5) | 0.95685 | 0.180639 | VLPALPQ (SEQ ID NO: 5) | 1.29 | 0.46 |
| | VLPALP (SEQ ID NO: 6) | 0.79994 | 0.060407 | VLPALP (SEQ ID NO: 6) | 1.39 | 0.25 |
| | LQGV (SEQ ID NO: 1) | 0.623505 | 0.04854 | LQGV (SEQ ID NO: 1) | 0.81 | 0.20 |
| | LQG | 0.604754 | | LQG | 1.91 | 0.80 |
| foam cells | None | 0.680602 | 0.118096 | none | 0.471046 | 0.074507 |
| | LAGV (SEQ ID NO: 4) | 0.628717 | 0.031388 | LAGV (SEQ ID NO: 4) | 1.34 | 0.19 |
| | AQGV (SEQ ID NO: 3) | 0.788278 | 0.120264 | AQGV (SEQ ID NO: 3) | 1.34 | 0.42 |
| | LAG | 0.564875 | 0.022564 | LAG | 0.91 | 0.10 |
| | AQG | 0.724893 | 0.06027 | AQG | 1.16 | 0.16 |
| | MTR | 0.801344 | 0.047998 | MTR | 0.99 | 0.05 |
| | MTRV (SEQ ID NO: 2) | 0.936911 | 0.309266 | MTRV (SEQ ID NO: 2) | 1.07 | 0.12 |
| | VLPALPQ (SEQ ID NO: 5) | 0.56192 | 0.028053 | VLPALPQ (SEQ ID NO: 5) | 1.01 | 0.17 |
| | VLPALP (SEQ ID NO: 6) | 0.745603 | 0.103929 | VLPALP (SEQ ID NO: 6) | 0.83 | 0.05 |
| | LQGV (SEQ ID NO: 1) | 0.682842 | 0.090676 | LQGV (SEQ ID NO: 1) | ND | |
| | LQG | 0.518613 | 0.032787 | LQG | 1.01 | 0.04 |

TABLE 6

Fold differences of selected chemokines as determined by Affymetrix microarray

| Chemokine | Effect of myelin ingestion | Additional effect of LAGV (SEQ ID NO: 4) | Additional effect of AQGV (SEQ ID NO: 3) | Additional effect of LQGV (SEQ ID NO: 1) |
|---|---|---|---|---|
| CCL2 | −1.6 | 3.27 | 5.3 | 3.1 |
| CCL3 | 2.5 | 1.1 | 1.1 | 1.0 |
| CCL4 | 3.3 | 1.3 | 1.4 | 1.1 |
| CCL5 | 4.3 | 1.4 | 2.1 | 1.7 |
| CCL7 | 1.6 | 1.6 | 2.5 | 1.9 |
| CXCL3 | 1.0 | 1.8 | 2.3 | 1.9 |
| CXCL8 | 5.1 | 1.5 | 2.0 | 1.8 |
| CCL18 | 3 | 2.8 | 4.5 | 3.3 |

TABLE 7a

Ranking of peptides as to suitability for treatment of MS

| | mean ranking | ranking a | ranking b | ranking c | ranking d |
|---|---|---|---|---|---|
| LQGV (SEQ ID NO: 1) | 2.25 | 1 | 2 | 3 | 3 |
| MTR | 4.25 | 3 | 6 | 1 | 7 |
| MTRV (SEQ ID NO: 2) | 5.25 | 8 | 3 | 4 | 6 |
| AQGV (SEQ ID NO: 3) | 5.5 | 4 | 8 | 8 | 2 |
| LAGV (SEQ ID NO: 4) | 5.5 | 6 | 5 | 10 | 1 |
| AQG | 5.75 | 2 | 9 | 9 | 3 |
| LQG | 6 | 7 | 1 | 6 | 10 |
| VLPALQ (SEQ ID NO: 5) | 6 | 9 | 4 | 2 | 9 |
| LAG | 6.25 | 5 | 7 | 5 | 8 |
| VLPALP (SEQ ID NO: 6) | 8 | 10 | 10 | 7 | 5 |

TABLE 7b

Ranking parameters

| | |
|---|---|
| A | lowest TNF foamy macrophages |
| B | highest IL-10 foamy macrophages |
| C | highest CCL18 macrophages |
| D | highest CCL18 foamy macrophages |

REFERENCES

Ares M. P., Stollenwerk M., Olsson A., Kallin B., Jovinge S., Nilsson J. Decreased inducibility of TNF expression in lipid-loaded macrophages. *BMC Immunol.* 2002; 3:13.

Autilio L. A., Norton W. T., Terry R. D. The Preparation and Some Properties of Purified Myelin from the Central Nervous System. *J. Neurochem.* 1964; 11: 17-27.

Becher B., Prat A., Antel J. P. Brain-immune connection: immuno-regulatory properties of CNS-resident cells. *Glia.* 2000; 29:293-304.

Cannella B., Raine C. S. Multiple sclerosis: Cytokine receptors on oligodendrocytes predict innate regulation. *Ann. Neurol.* 2004; 55:46-57.

Chayen J., Bitensky L. Analysis of chemical components of cells and tissues; reactions for lipids. *Practical Histochemistry*. West Sussex: Wiley, 1991:45.

Goerdt S., Politz O., Schledzewski K., Birk R., Gratchev A., Guillot P., et al. Alternative versus classical activation of macrophages. *Pathobiology* 1999; 67:222-6.

Gordon S. Alternative activation of macrophages. *Nat. Rev. Immunol.* 2003; 3:23-35.

Gratchev A., Schledzewski K., Guillot P., Goerdt S. Alternatively activated antigen-presenting cells: molecular repertoire, immune regulation, and healing. *Skin Pharmacol. Appl. Skin Physiol.* 2001; 14:272-9.

Greaves D. R., Gordon S. Thematic review series: The Immune System and Atherogenesis. Recent insights into the biology of macrophage scavenger receptors. *J. Lipid Res.* 2005; 46:11-20.

Greter M., Heppner F. L., Lemos M. P., Odermatt B. M., Goebels N., Laufer T., et al. Dendritic cells permit immune invasion of the CNS in an animal model of multiple sclerosis. *Nat. Med.* 2005; 11:328-34.

Grigoriadis N., Ben-Hur T., Karussis D., Milonas I. Axonal damage in multiple sclerosis: a complex issue in a complex disease. *Clin. Neurol. Neurosurg.* 2004; 106:211-7.

Harris S. G., Padilla J., Koumas L., Ray D., Phipps R. P. Prostaglandins as modulators of immunity. *Trends Immunol.* 2002; 23:144-50.

Heppner F. L., Greter M., Marino D., Falsig J., Raivich G., Hovelmeyer N., et al. Experimental autoimmune encephalomyelitis repressed by microglial paralysis. *Nat. Med.* 2005; 11:146-52.

Hinz B., Brune K., Pahl A. Prostaglandin E(2) upregulates cyclooxygenase-2 expression in lipopolysaccharide-stimulated RAW 264.7 macrophages. *Biochem. Biophys. Res. Commun.* 2000; 272: 744-8.

Hoefakker S., Boersma W. J., Claassen E. Detection of human cytokines in situ using antibody and probe based methods. *J. Immunol. Methods* 1995; 185:149-75.

Ikegami R., Sugimoto Y., Segi E., Katsuyama M., Karahashi H., Amano F., et al. The expression of prostaglandin E receptors EP2 and EP4 and their different regulation by lipopolysaccharide in C3H/HeN peritoneal macrophages. *J. Immunol.* 2001; 166:4689-96.

Joseph S. B., Bradley M. N., Castrillo A., Bruhn K. W., Mak P. A., Pei L., et al. LXR-dependent gene expression is important for macrophage survival and the innate immune response. *Cell* 2004; 119:299-309.

Joseph S. B., Castrillo A., Laffitte B. A., Mangelsdorf D. J., Tontonoz P. Reciprocal regulation of inflammation and lipid metabolism by liver X receptors. *Nat. Med.* 2003; 9:213-9.

Kalinski P., Hilkens C. M., Snijders A., Snijdewint F. G., Kapsenberg M. L. Dendritic cells, obtained from peripheral blood precursors in the presence of PGE2, promote Th2 responses. *Adv. Exp. Med. Biol.* 1997; 417:363-7.

Kodelja V., Muller C., Politz O., Hakij N., Orfanos C. E., Goerdt S. Alternative macrophage activation-associated CC-chemokine-1, a novel structural homologue of macrophage inflammatory protein-1 alpha with a Th2-associated expression pattern. *J. Immunol.* 1998; 160:1411-8.

Kuhlmann T., Lingfeld G., Bitsch A., Schuchardt J., Bruck W. Acute axonal damage in multiple sclerosis is most extensive in early disease stages and decreases over time. *Brain* 2002; 125:2202-12.

Lassmann H. Recent neuropathological findings in MS—implications for diagnosis and therapy. *J. Neurol.* 2004; 251 Suppl. 4:IV2-5.

Lawrence T., Willoughby D. A., Gilroy D. W. Anti-inflammatory lipid mediators and insights into the resolution of inflammation. *Nat. Rev. Immunol.* 2002; 2:787-95.

Li H., Cuzner M. L., Newcombe J. Microglia-derived macrophages in early multiple sclerosis plaques. *Neuropathol. Appl. Neurobiol.* 1996; 22:207-15.

Lo C. J., Fu M., Lo F. R., Cryer H. G. Macrophage TNF mRNA expression induced by LPS is regulated by sphingomyelin metabolites. *Shock* 1999; 11:411-5.

Mantovani A., Sica A., Sozzani S., Allavena P., Vecchi A., Locati M. The chemokine system in diverse forms of macrophage activation and polarization. *Trends Immunol.* 2004; 25:677-86.

Mantovani A., Sozzani S., Locati M., Allavena P., Sica A. Macrophage polarization: tumor-associated macrophages as a paradigm for polarized M2 mononuclear phagocytes. *Trends Immunol.* 2002; 23:549-55.

Matute C., Perez-Cerda F. Multiple sclerosis: novel perspectives on newly forming lesions. *Trends Neurosci.* 2005; 28:173-5.

McMahon E. J., Bailey S. L., Castenada C. V., Waldner H., Miller S. D. Epitope spreading initiates in the CNS in two mouse models of multiple sclerosis. *Nat. Med.* 2005; 11:335-339.

Mosser D. M. The many faces of macrophage activation. *J. Leukoc. Biol.* 2003; 73:209-12.

Newcombe J., Li H., Cuzner M. L. Low density lipoprotein uptake by macrophages in multiple sclerosis plaques: implications for pathogenesis. *Neuropathol. Appl. Neurobiol.* 1994; 20:152-62.

Norton W. T., Poduslo S. E. Myelination in rat brain: method of myelin isolation. *J. Neurochem.* 1973; 21:749-57.

Pettus B. J., Chalfant C. E., Hannun Y. A. Ceramide in apoptosis: an overview and current perspectives. *Biochim. Biophys. Acta* 2002; 1585:114-25.

Platten M., Steinman L. Multiple sclerosis: trapped in deadly glue. *Nat. Med.* 2005; 11:252-3.

Raine C. S. Multiple sclerosis: immune system molecule expression in the central nervous system. *J. Neuropathol. Exp. Neurol.* 1994; 53:328-37.

Sospedra M., Martin R. Immunology of multiple sclerosis *. *Annu. Rev. Immunol.* 2005; 23:683-747.

van der Fits L., van der Wel L. I., Laman J. D., Prens E. P., Verschuren M. C. Psoriatic lesional skin exhibits an aberrant expression pattern of interferon regulatory factor-2 (IRF-2). *J. Pathol.* 2003; 199:107-14.

van der Laan L. J., Ruuls S. R., Weber K. S., Lodder I. J., Dopp E. A., Dijkstra C. D. Macrophage phagocytosis of myelin in vitro determined by flow cytometry: phagocytosis is mediated by CR3 and induces production of tumor necrosis factor-alpha and nitric oxide. *J. Neuroimmunol.* 1996; 70:145-52.

Varadhachary A. S., Monestier M., Salgame P. Reciprocal induction of IL-10 and IL-12 from macrophages by low-density lipoprotein and its oxidized forms. *Cell Immunol.* 2001; 213:45-51.

Vulcano M., Struyf S., Scapini P., Cassatella M., Bernasconi S., Bonecchi R., et al. Unique regulation of CCL18 production by maturing dendritic cells. *J. Immunol.* 2003; 170:3843-9.

Wingerchuk D. M., Lucchinetti C. F., Noseworthy J. H. Multiple sclerosis: current pathophysiological concepts. *Lab Invest.* 2001; 81:263-81.

Woelk H., Borri P. Lipid and fatty acid composition of myelin purified from normal and MS brains. *Eur. Neurol.* 1973; 10:250-60.

What is claimed is:

1. A method for the treatment of exacerbations resulting from pro-inflammatory cytokine release in a subject having multiple sclerosis, said method comprising:
   administering to the subject, in an amount sufficient to reduce NF-kappaB mediated inflammatory cytokine release, a pharmaceutical composition comprising LQGV (SEQ ID NO: 1), MTR, MTRV (SEQ ID NO: 2), AQGV (SEQ ID NO: 3), LAGV (SEQ ID NO: 4), AQG, LQG, VLPALPQ (SEQ ID NO: 5), LAG, and/or VLPALP (SEQ ID NO: 6).

2. The method according to claim 1, wherein said pharmaceutical composition comprises LQGV (SEQ ID NO: 1), MTR, MTRV (SEQ ID NO: 2), AQGV (SEQ ID NO: 3), LAGV (SEQ ID NO: 4), AQG, and/or LQG.

3. The method according to claim 2, wherein said pharmaceutical composition comprises LQGV (SEQ ID NO: 1), MTR, and/or MTRV (SEQ ID NO: 2).

4. The method according to claim 3, wherein said pharmaceutical composition consists essentially of LQGV (SEQ ID NO: 1) together with a pharmaceutically acceptable diluent.

* * * * *